United States Patent
Aeschlimann et al.

(10) Patent No.: US 9,724,206 B2
(45) Date of Patent: Aug. 8, 2017

(54) DEVICE TO BE IMPLANTED IN HUMAN OR ANIMAL TISSUE AND METHOD FOR IMPLANTING AND ASSEMBLING THE DEVICE

(75) Inventors: Marcel Aeschlimann, Ligerz (CH); Laurent Torriani, Lamboing (CH); Andrea Muller, Winterthur (CH); Thomas Knecht, Hausen (CH); Philipp Seiler, Niederdorf (CH); Urs Weber, Evilard (CH); Christopher Rast, Biel (CH); Jorg Mayer, Niederlenz (CH); Stephanie Mehl, Zug (CH); Milica Berra, Schlieren (CH)

(73) Assignee: WOODWELDING AG, Stansstad (CH)

( * ) Notice: Subject to any disclaimer, the term of this patent is extended or adjusted under 35 U.S.C. 154(b) by 1762 days.

(21) Appl. No.: 12/442,328

(22) PCT Filed: Sep. 19, 2007

(86) PCT No.: PCT/CH2007/000458
§ 371 (c)(1),
(2), (4) Date: Sep. 21, 2009

(87) PCT Pub. No.: WO2008/034276
PCT Pub. Date: Mar. 27, 2008

(65) Prior Publication Data
US 2010/0023057 A1    Jan. 28, 2010

Related U.S. Application Data

(60) Provisional application No. 60/826,296, filed on Sep. 20, 2006.

(51) Int. Cl.
*A61F 2/44*      (2006.01)
*A61B 17/04*    (2006.01)
(Continued)

(52) U.S. Cl.
CPC ........ *A61F 2/4455* (2013.01); *A61B 17/0401* (2013.01); *A61B 17/0642* (2013.01);
(Continued)

(58) Field of Classification Search
USPC ..................... 606/279, 92–94, 914
See application file for complete search history.

(56) References Cited

U.S. PATENT DOCUMENTS

| | | |
|---|---|---|
| 5,163,960 A | 11/1992 | Bonutti |
| 5,584,693 A | 12/1996 | Nishihara |

(Continued)

FOREIGN PATENT DOCUMENTS

| | | |
|---|---|---|
| JP | 07222752 | 8/1995 |
| JP | 2005538761 | 12/2005 |

(Continued)

*Primary Examiner* — David Bates
*Assistant Examiner* — Olivia C Chang
(74) *Attorney, Agent, or Firm* — Rankin, Hill & Clark LLP

(57) ABSTRACT

An implant or endoprosthesis suitable to be implanted in human or animal tissue includes two (or more than two) parts to be joined in situ. Each one of the parts includes a joining location, the two joining locations facing each other when the device parts are positioned for being joined together, wherein one of the joining locations includes a material which is liquefiable by mechanical vibration and the other one of the joining locations includes a material which is not liquefiable by mechanical vibration and a structure (e.g. undercut cavities or protrusions) suitable for forming a positive fit connection with the liquefiable material. The joining process is effected by pressing the two device parts against each other and by applying ultrasonic vibration to one of the device parts when the two parts are positioned relative to each other such that the two joining locations are in contact with each other.

17 Claims, 17 Drawing Sheets

(51) Int. Cl.

| | | |
|---|---|---|
| *A61B 17/064* | (2006.01) | |
| *A61B 17/64* | (2006.01) | |
| *A61B 17/68* | (2006.01) | |
| *A61B 17/70* | (2006.01) | |
| *A61B 17/72* | (2006.01) | |
| *A61B 17/88* | (2006.01) | |
| *A61F 2/08* | (2006.01) | |
| *A61F 2/30* | (2006.01) | |
| *A61F 2/40* | (2006.01) | |
| *A61F 2/42* | (2006.01) | |
| *A61B 17/80* | (2006.01) | |
| *A61B 17/00* | (2006.01) | |
| *A61C 8/00* | (2006.01) | |
| *A61F 2/28* | (2006.01) | |
| *A61F 2/32* | (2006.01) | |
| *A61F 2/34* | (2006.01) | |
| *A61F 2/36* | (2006.01) | |
| *A61F 2/38* | (2006.01) | |
| *A61F 2/46* | (2006.01) | |

(52) U.S. Cl.
CPC .......... *A61B 17/6466* (2013.01); *A61B 17/68* (2013.01); *A61B 17/70* (2013.01); *A61B 17/725* (2013.01); *A61B 17/7233* (2013.01); *A61B 17/7258* (2013.01); *A61B 17/8004* (2013.01); *A61B 17/8047* (2013.01); *A61B 17/8822* (2013.01); *A61F 2/0811* (2013.01); *A61F 2/30734* (2013.01); *A61F 2/30749* (2013.01); *A61F 2/30767* (2013.01); *A61F 2/3601* (2013.01); *A61F 2/40* (2013.01); *A61F 2/42* (2013.01); *A61F 2/442* (2013.01); *A61F 2/4405* (2013.01); *A61F 2/4601* (2013.01); *A61F 2/4611* (2013.01); *A61B 17/7098* (2013.01); *A61B 17/7291* (2013.01); *A61B 17/80* (2013.01); *A61B 2017/00955* (2013.01); *A61B 2017/0409* (2013.01); *A61B 2017/0414* (2013.01); *A61C 8/0012* (2013.01); *A61C 8/0016* (2013.01); *A61C 8/0018* (2013.01); *A61F 2/28* (2013.01); *A61F 2/32* (2013.01); *A61F 2/34* (2013.01); *A61F 2/36* (2013.01); *A61F 2/367* (2013.01); *A61F 2/3609* (2013.01); *A61F 2/3662* (2013.01); *A61F 2/3676* (2013.01); *A61F 2/389* (2013.01); *A61F 2/4225* (2013.01); *A61F 2/4241* (2013.01); *A61F 2002/0823* (2013.01); *A61F 2002/0864* (2013.01); *A61F 2002/0888* (2013.01); *A61F 2002/2835* (2013.01); *A61F 2002/30062* (2013.01); *A61F 2002/30065* (2013.01); *A61F 2002/30067* (2013.01); *A61F 2002/3092* (2013.01); *A61F 2002/30133* (2013.01); *A61F 2002/30166* (2013.01); *A61F 2002/30329* (2013.01); *A61F 2002/30331* (2013.01); *A61F 2002/30332* (2013.01); *A61F 2002/30344* (2013.01); *A61F 2002/30378* (2013.01); *A61F 2002/30387* (2013.01); *A61F 2002/30448* (2013.01); *A61F 2002/30457* (2013.01); *A61F 2002/30471* (2013.01); *A61F 2002/30474* (2013.01); *A61F 2002/30477* (2013.01); *A61F 2002/30485* (2013.01); *A61F 2002/30599* (2013.01); *A61F 2002/30604* (2013.01); *A61F 2002/30612* (2013.01); *A61F 2002/30736* (2013.01); *A61F 2002/30738* (2013.01); *A61F 2002/30823* (2013.01); *A61F 2002/30958* (2013.01); *A61F 2002/30968* (2013.01); *A61F 2002/30973* (2013.01); *A61F 2002/3631* (2013.01); *A61F 2002/3652* (2013.01); *A61F 2002/3674* (2013.01); *A61F 2002/4066* (2013.01); *A61F 2002/4415* (2013.01); *A61F 2002/4475* (2013.01); *A61F 2002/4631* (2013.01); *A61F 2002/4635* (2013.01); *A61F 2002/4683* (2013.01); *A61F 2210/0004* (2013.01); *A61F 2210/0071* (2013.01); *A61F 2220/005* (2013.01); *A61F 2220/0008* (2013.01); *A61F 2220/0025* (2013.01); *A61F 2220/0033* (2013.01); *A61F 2220/0058* (2013.01); *A61F 2220/0091* (2013.01); *A61F 2230/0015* (2013.01); *A61F 2230/0028* (2013.01); *A61F 2250/0063* (2013.01); *A61F 2310/00023* (2013.01); *A61F 2310/00359* (2013.01); *A61F 2310/00407* (2013.01)

(56) References Cited

U.S. PATENT DOCUMENTS

| | | |
|---|---|---|
| 5,593,425 A | 1/1997 | Bonutti et al. |
| 5,941,901 A | 8/1999 | Egan |
| 6,056,751 A | 5/2000 | Fenton, Jr. |
| 6,174,324 B1 | 1/2001 | Egan et al. |
| 6,368,343 B1 | 4/2002 | Bonutti et al. |
| 6,605,090 B1 | 8/2003 | Trieu et al. |
| 6,635,073 B2 | 10/2003 | Bonutti |
| 6,972,019 B2 * | 12/2005 | Michelson ............... 606/86 A |
| 7,001,411 B1 | 2/2006 | Dean |
| 7,008,226 B2 | 3/2006 | Mayer et al. |
| 7,335,205 B2 | 2/2008 | Aeschlimann et al. |
| 2004/0030341 A1 * | 2/2004 | Aeschlimann et al. ........ 606/72 |
| 2005/0228498 A1 | 10/2005 | Andres |
| 2006/0058876 A1 | 3/2006 | McKinley |
| 2006/0105295 A1 | 5/2006 | Mayer et al. |
| 2007/0270833 A1 | 11/2007 | Bonutti et al. |
| 2008/0021474 A1 | 1/2008 | Bonutti et al. |
| 2008/0039845 A1 | 2/2008 | Bonutti et al. |
| 2008/0260398 A1 | 10/2008 | Itoh |
| 2009/0018581 A1 | 1/2009 | Anderson et al. |
| 2009/0024161 A1 | 1/2009 | Bonutti et al. |
| 2010/0211120 A1 | 8/2010 | Bonutti et al. |
| 2012/0030059 A1 | 2/2012 | McCormick |
| 2012/0288323 A1 | 11/2012 | Salvador |
| 2012/0290096 A1 | 11/2012 | Messerli |
| 2012/0303059 A1 | 11/2012 | Saadat |
| 2012/0310352 A1 | 12/2012 | DiMauro |
| 2012/0310355 A1 | 12/2012 | Dutoit |
| 2013/0018478 A1 | 1/2013 | Hanssen |

FOREIGN PATENT DOCUMENTS

| | | |
|---|---|---|
| WO | 02/069817 | 9/2002 |
| WO | 02/069817 A1 | 9/2002 |
| WO | 2004/017857 | 3/2004 |
| WO | 2004/017857 A1 | 3/2004 |
| WO | 2004/098423 | 11/2004 |
| WO | 2005/048897 | 6/2005 |
| WO | 2005/079696 | 9/2005 |
| WO | 2005/079696 A1 | 9/2005 |
| WO | 2006/047587 | 5/2006 |
| WO | 2008/116203 A2 | 9/2008 |

* cited by examiner

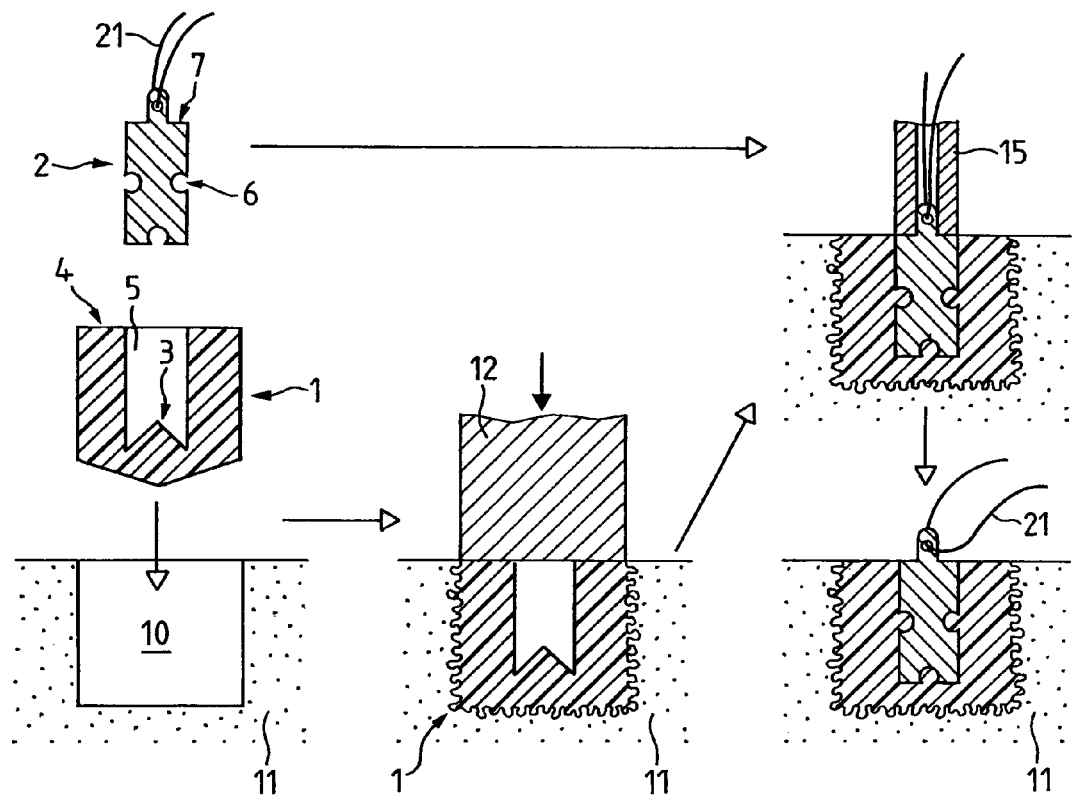
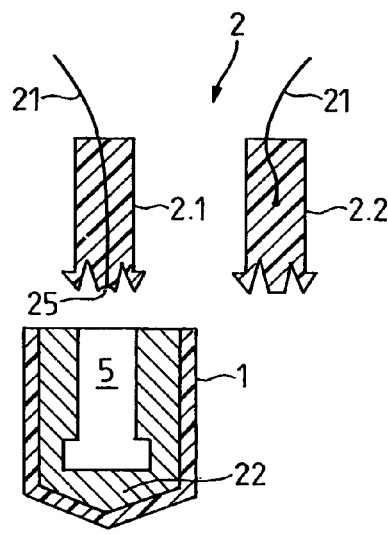 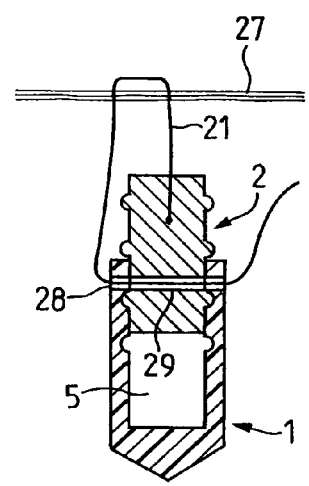
Fig. 9          Fig. 10

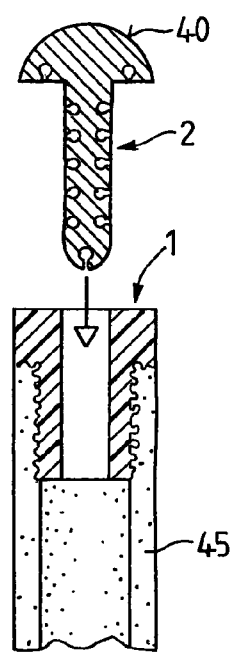
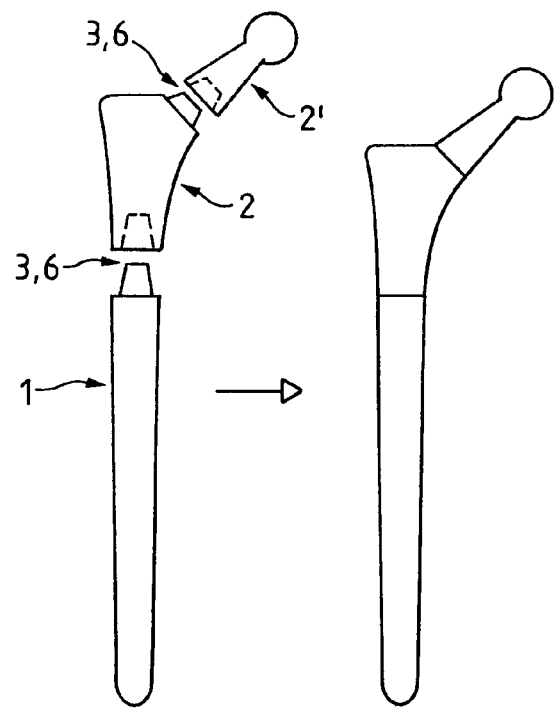
Fig. 15　　　　　Fig. 16
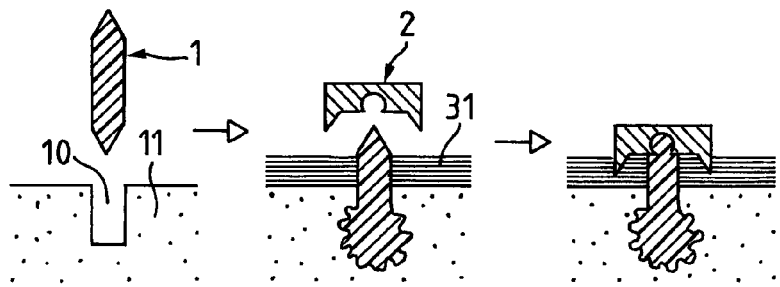
Fig. 17
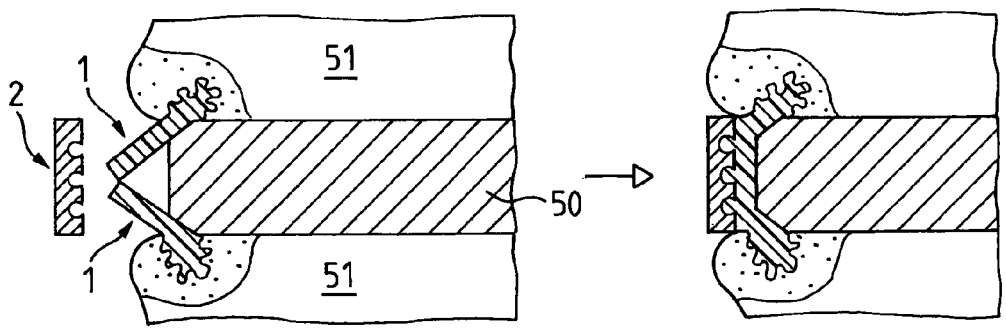
Fig. 18

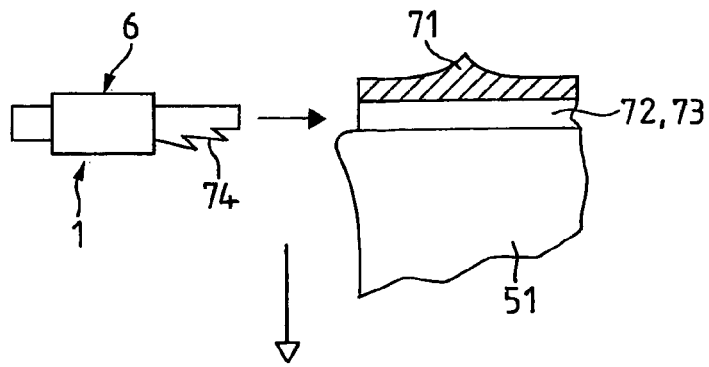
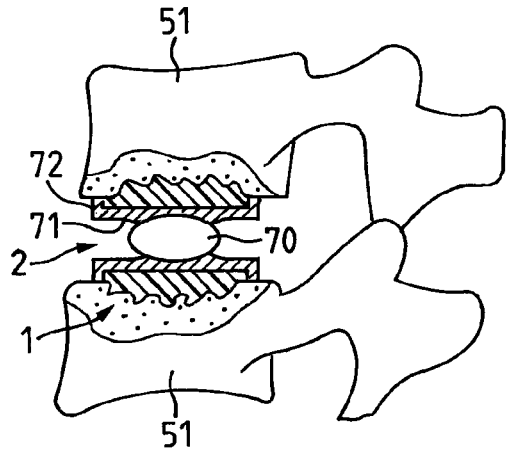
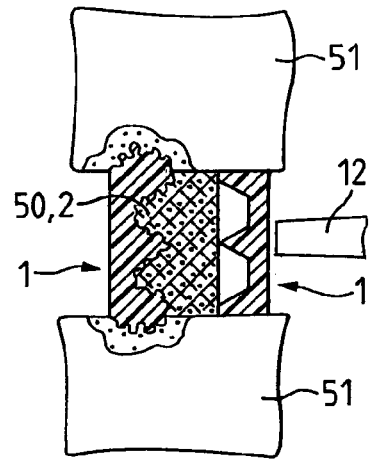
Fig. 30
Fig. 31
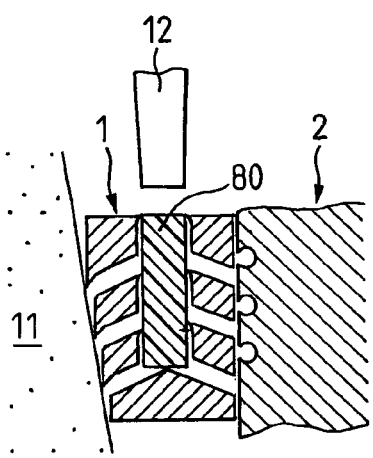
Fig. 32

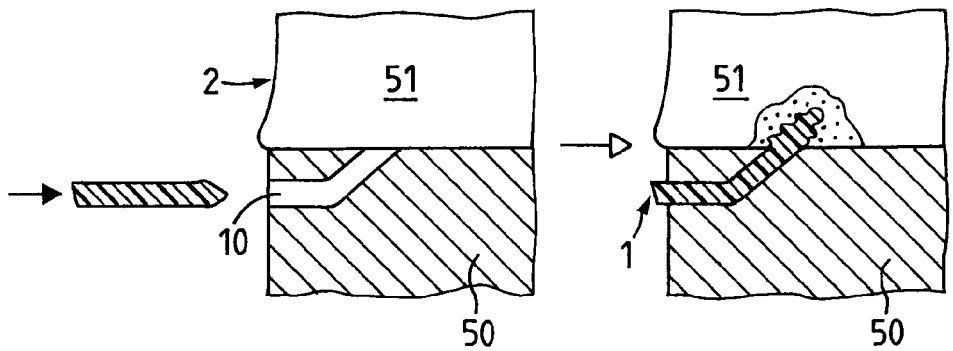
Fig. 48
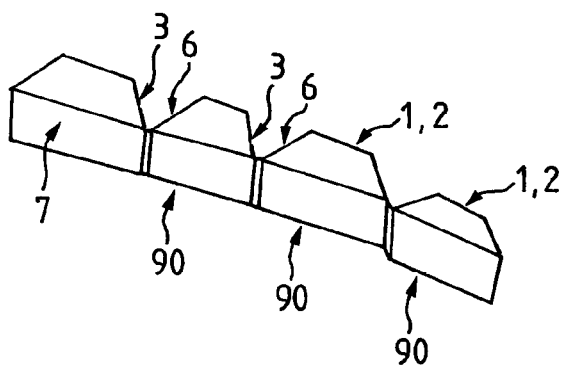
Fig. 49
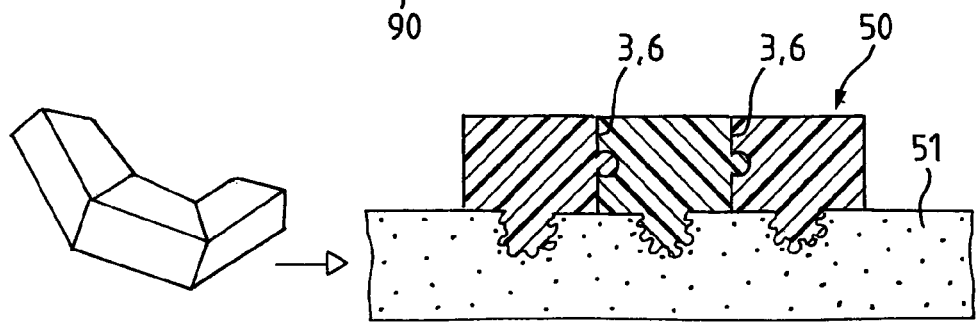
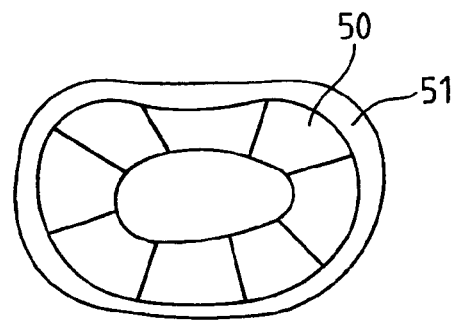
Fig. 50

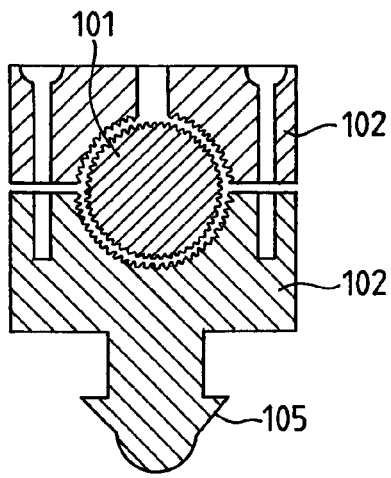
Fig. 57
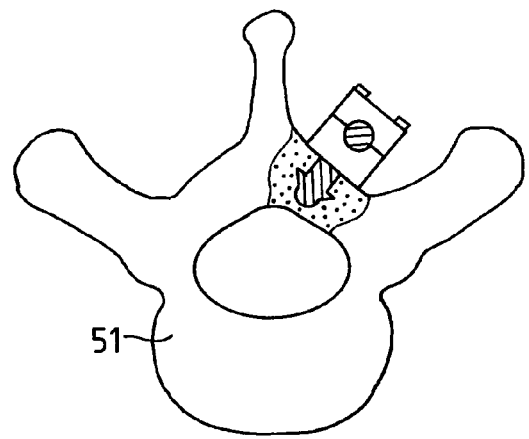
Fig. 58
Fig. 59
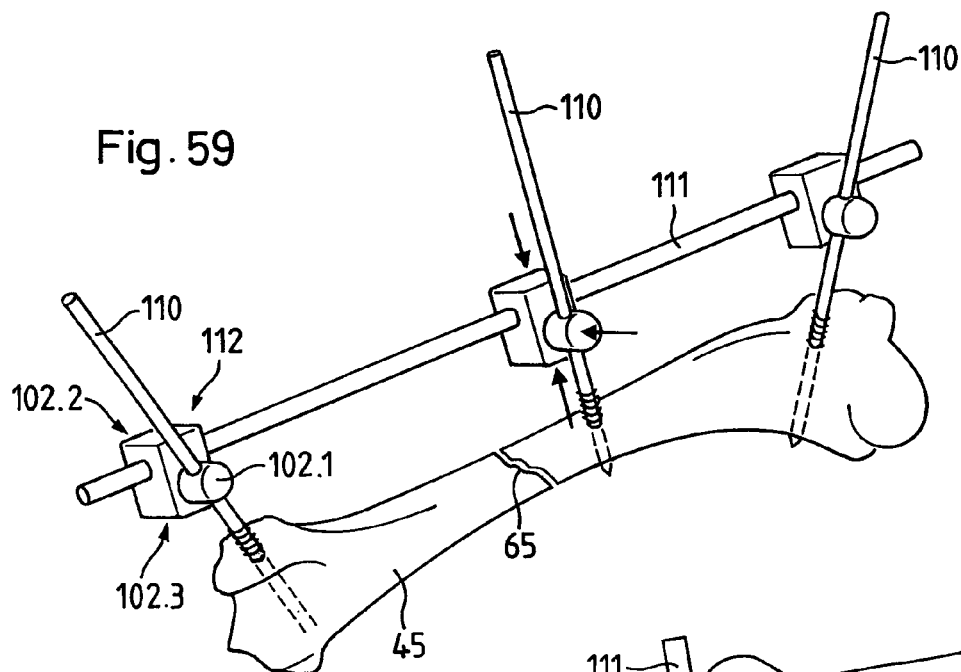
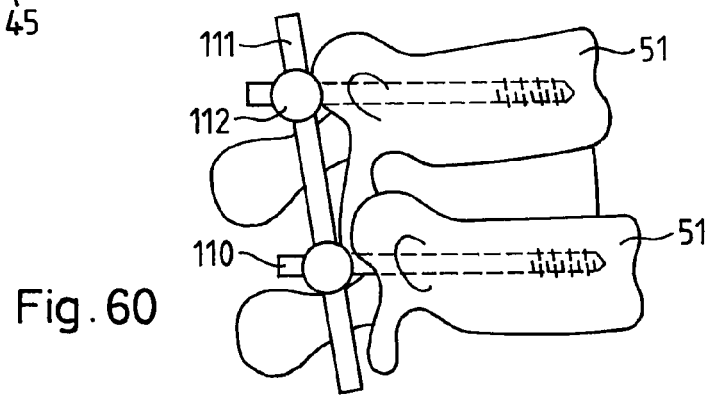
Fig. 60

DEVICE TO BE IMPLANTED IN HUMAN OR ANIMAL TISSUE AND METHOD FOR IMPLANTING AND ASSEMBLING THE DEVICE

The invention is in the field of medical technology and concerns a device to be implanted in human or animal tissue, i.e. an implant or endoprosthesis. The device comprises two or more than two device parts which are equipped for in situ assembly, i.e. to be joined during the implantation operation and in the implantation site. The invention further concerns a method for implanting and assembling the device in a human or animal patient, in particular implanting it in bone tissue of the patient.

According to the state of the art, implants or endoprostheses consist of metallic, ceramic or polymer materials. Some known implants or endoprotheses comprise a plurality of parts which are assembled either when being manufactured or immediately before implantation and before being positioned in the implantation site (ex situ assembly). The parts e.g. consist of different materials and form implant regions having different functions, as e.g. described in the publications WO 2004/017857 or WO 2005/079696. The parts may also come in sets comprising a selection of part shapes or part sizes, wherein parts are chosen and assembled immediately before implantation (ex situ) to fit the individual implantation site (described e.g. in U.S. Pat. No. 5,593,425, Bonutti). Furthermore, it is known to fix a further part to the proximal end of an implanted implant or endoprosthesis (in situ assembly) which further part then protrudes from the tissue in which the implant or endoposthesis is implanted (e.g. crown mounted on a dental implant or ball mounted on the shaft of a hip joint prosthesis). It is further known to secure implants or endoprostheses which are implanted in the tissue by further implants (e.g. cross pins for securing the shaft of an endoprosthesis shaft). The known in situ assemblies are usually based on a bore in one of the parts and a corresponding bolt, cone or screw on the other part. Due to the named assembly means the freedom which these assemblies can offer regarding selectable relative positions for the assembled parts and therefore their applications are very limited. In the above mentioned publication U.S. Pat. No. 5,593,425 it is suggested to assemble endoprosthesis parts, of which one comprises a thermoplastic material, by heating this thermoplastic material and therewith make its surface tacky and to bring the heated and therewith tacky surface in contact with a non-thermoplastic surface of an other endoprosthesis part in order to adhere it there. This method allows more freedom of relative placement of the endoprosthesis parts relative to each other, but the strength of the resulting connection is limited.

It is the object of the invention to create a device to be implanted in a human or animal patient, the device being an implant or endoprosthesis and comprising at least two parts to be assembled in situ. It is a further object of the invention to create a method for implanting and assembling the device. The device and the method according to the invention are to be more universally applicable than known multi-part implants or prostheses for in situ assembly and are to allow more flexibility regarding the relative position of the assembled parts relative to each other, but still resulting in a strong connection between the implant or prosthesis parts.

This object is achieve by the device and the method according to the invention.

The device according to the invention comprises two (or more than two) parts which parts are equipped for being assembled, i.e. joined together, using mechanical oscillation, in particular ultrasonic vibration, which is applied to one of the parts by contacting this part with a mechanically vibrating tool. The device parts usually consist of an artificial material but some of the parts may also consist of bone tissue. Each one of the two parts of the device comprises a joining location, the two joining locations being matched to each other for being in contact with each other when the parts are positioned to be joined and for being connected to each other after the joining process, wherein the resulting joint is a positive fit connection.

For achieving a positive fit connection, a first one of each matched pair of joining locations comprises a material having thermoplastic properties and being liquefiable by mechanical vibration, which material forms the surface of the joining location or can be pressed to this surface from the inside of the part by application of the mechanical vibration. A second one of each pair of matched joining locations comprises a material which is not liquefiable by the mechanical vibration to be used for joining the two device parts (e.g. metal, ceramic material or polymer with duroplastic properties or with thermoplastic properties but with a melting temperature which is relevantly higher than the melting temperature of the liquefiable material) and it further comprises a structure being suitable for a positive fit connection with the material of the first joining location when this material is liquefied, made to penetrate into the structure and to re-solidify within this structure. The structure of the second joining location comprises an undercut cavity or protrusion or a plurality of undercut cavities or protrusions, wherein one or a relatively small number of cavities (e.g. bores or grooves) or protrusions having a defined form and a size of preferably a few mm is provided and/or a large number of cavities and protrusions having random forms, i.e. being formed by e.g. an open-porous surface material or a surface coating consisting of assembled particles (e.g. sintered material). For enabling penetration of the surface structures by the liquefied material of the first joining location and for realizing a stable joint, the cavities of the porous or particulate surface material need to have a size of at least about 0.3 mm and the surface structure needs to have a depth which is at least twice as large as the fineness of the structure (pore size of the porous material, particle size of the particulate coating).

At least one of the device parts to be joined together further comprises a contact location in which it is able to be contacted with a vibrating tool (e.g. sonotrode of an ultrasonic device) for the joining process. The part comprising the contact location may comprise the first or the second joining location.

At least the device part comprising the contact location and preferably both device parts are designed as mechanically stable oscillators such that mechanical vibration applied to the contact location is transmitted by the oscillator to the joining location with as little damping loss as possible and in particular without reduction of the mechanical stability of the oscillator during the application such that it becomes possible to liquefy enough (but not more) material in the region of the joining locations for achieving the desired positive fit connection but without further changing form or material of the device part. For achieving good oscillator properties the device parts are made of materials having an elasticity module of at least about 0.5 GPa for low damping losses. The surface of either joining location is preferably equipped with protruding energy directors (protruding pyramids, cones, combs etc. having a height of at least 10 µm) which, on application of the vibration, locally concentrate the vibrational energy such causing high local shearing stresses and therefore local and fast liquefaction of the surface material even if the melting point of this material is as high as 200 to 450° C. By such local liquefaction, the amount of material which is liquefied can be kept small (e.g. just enough for penetrating the structure of the second joining location) and therefore the thermal loading of the tissue remains within physiologic limits (allowing for functional regeneration of the tissue) even when macroscopic cavities of the second joining location need to be filled with the liquefied material.

Depending on the form of the two joining locations, the liquefied material may allow adjustments of the relative position of the two device parts during the joining process, which makes it possible to in situ adapt the relative position of the two device parts to the implant site. Larger such in situ adaptation is made possible, if at least one of the joining locations is designed such that it allows joining of the two parts in a selected one of a plurality of different possible relative positions.

According to some aspects of the invention, at least one part of the device or both parts of the device are positioned and possibly fixed in the tissue, the two parts are positioned relative to each other such that their joining locations are in contact with each other and then the mechanical vibration is applied to either one of the parts for joining the two parts by liquefying the liquefiable material of the first joining location, by making it to penetrate into the cavity or cavities or between and under the protrusion or protrusions of the second joining location and letting it re-solidify there. The mechanical vibration used for joining the device parts has e.g. a frequency of 2 to 200 kHz and is preferably ultrasonic vibration.

For fixing the device parts to the tissue per se known methods, such as e.g. screwing, clamping, pinning, cementing, suturing or press-fitting are applicable. According to preferred embodiments of the method according to the invention the application of mechanical vibration is used not only for joining the two device parts together but also for fixing one or both of the device parts in the tissue by anchoring it in the tissue (in particular in bone tissue) with the aid of a liquefiable material. The two applications of mechanical vibration may be carried out simultaneously and using the same contact location and the same vibrating tool and/or in succession and using different contact locations and the same tool or different tools.

Devices to be anchored in tissue, in particular in bone tissue, with the aid of a liquefiable material and mechanical vibration and methods for implanting such devices are described in the publications WO 2002/069817, WO 2004/017857 or WO 2005/079696, the disclosure of these publications being enclosed herein by reference.

Experiments show that successful anchorage effected simultaneously with the joining is easily effected for the device part to which the vibration is applied, and anchorage effected before the joining is easier conserved when the subsequent vibration for the joining process is not applied to the anchored device part. These findings are due to the fact that transmission of the vibration through the joining locations being in contact with each other is hardly possible as the liquefiable material being present where the two joining locations are in contact is liquefied substantially immediately on application of the vibration such that hardly any vibrational energy can be transmitted through the joining locations. This means that beyond the joining locations hardly any liquefaction by mechanical vibration occurs and therefore neither anchorage in tissue with the aid of liquefiable material and mechanical vibration nor damaging such anchorage can be effected.

In the present text the term "liquefiable material" is used for a material comprised by the device which material can be liquefied by mechanical vibration, e.g. by ultrasonic vibration. If the liquefiable material is to take over load-bearing functions and/or if only a very limited amount thereof at predetermined locations is to be liquefied, the liquefiable material is a material in which the mechanical vibration causes no internal stress strong enough for plastifying or liquefying the material but on whose surface such liquefaction can be effected by contact with a non-vibrating element, wherein such contact is limited to points or lines (energy directors). Such materials are materials having thermoplastic properties and an elasticity module of at least 0.5 GPa. If the liquefiable material is not to have a load-bearing function and/or if more of the material is to be liquefied by the mechanical vibration, the liquefiable material may be a material as above described but may also be a material with thermoplastic properties and with a smaller elasticity module.

In the present text the term "non-liquefiable material" is used for an additional material comprised by the device. In the non-liquefiable material mechanical vibration, e.g. ultrasonic vibration, as used for liquefaction of the liquefiable material, causes no internal stress which is strong enough for liquefying the material nor is such vibration able to liquefy the non-liquefiable material in surface areas being in contact with a non-vibrating element even if such contact is limited to single points or lines (energy directors).

From the above follows that the properties of the non-liquefiable material of a specific device depend on the properties of the liquefiable material of the same device. Generally speaking: the less vibrational energy is used for liquefaction of enough of the liquefiable material, the easier liquefiable the non-liquefiable material may be. Therefore a thermoplastic material with a high melting temperature (e.g. PEEK) is suitable to be used as non-liquefiable material if the liquefiable material is e.g. PLLA. On the other hand the same thermoplastic material (e.g. PEEK) is suitable as liquefiable material if the non-liquefiable material is e.g. titanium or a ceramic material.

In the present text the term "mechanically stable oscillator" is used for a body which is able to be vibrated by e.g. ultrasonic vibration without being internally affected by the vibration. A mechanically stable oscillator comprises no form element which is deformed by the vibration, it comprises no material with a high damping loss (e.g. elasticity module considerably less than 0.5 GPa) and, if it comprises more than one part, the parts are joined such that vibration passes through the joint substantially without loss or reflection.

In the present text the terms "bone tissue" or "bone" are used to encompass not only viable bone tissue but also bone replacement material.

The invention comprises aspects A to E as detailed below.

Aspect A: The first device part forms a base in bone tissue for the second device part. The base part is equipped for being anchored in bone tissue with the aid of a liquefiable material and mechanical vibration and preferably comprises the first joining location. A distal end of the second device part (based part), is to be fixed to the bone tissue via the base part and preferably comprises the second joining location. The base part is anchored in the bone tissue by mechanical vibration and the based part is joined to the base part again by mechanical vibration. Depending on the specific design of base part and based part, anchorage of the base part in the bone tissue and joining of the based part thereto are carried out in two successive steps, wherein the vibration is first applied to the base part and then to the based part, or in one step, wherein the vibration is applied to the base part.

Aspect B: The first device part is again a base part equipped for being anchored in bone tissue with the aid of a liquefiable material and mechanical vibration. The base part is pin-, plate- or possibly wedge-shaped and preferably comprises the first joining location, the based part (second device part) preferably comprising the second joining location. For fixing the device to bone tissue, the based part is positioned relative to the bone tissue, its joining location facing the bone tissue. The base element is then pushed between the bone tissue and the based part and simultaneously mechanical vibration is applied to its proximal end, such that on one of its lateral sides the base part is anchored in the bone tissue and on an opposite lateral side it is joined to the based part, thereby fixing the based part relative to the bone tissue. A similar method can be used for fixing instead of a device part (based part) to bone tissue, a device part to another device part or a bone tissue part to another bone tissue part (e.g. bone fragments).

Aspect C: The first device part is again a preferably pin- or plate-shaped base part equipped for being anchored in bone tissue with the aid of a liquefiable material and mechanical vibration and preferably comprising the first joining location, the second device part (based part) preferably comprising the second joining location. A tunnel is provided in the bone tissue, the second device part is positioned adjoining a distal tunnel mouth and the base part is brought through the proximal tunnel mouth into the tunnel and at the distal tunnel mouth in contact with the joining location of the based part. Base part and based part are then joined together in the region of the distal tunnel mouth by applying mechanical vibration to the base part near the proximal tunnel mouth, wherein simultaneously with the joining of the two device parts, the base part is anchored in the bone tissue of the tunnel walls. The base part may be fixed to the bone tissue by other means than anchorage with the aid of a liquefiable material and mechanical vibration. Instead of in bone tissue, the tunnel may also be provided in a further device part.

Aspect D: a plurality of device parts is pre-assembled such that the device parts are movable relative to each other in a limited way. Selected ones of the device parts may be equipped for being anchored in bone tissue with the aid of a liquefiable material and mechanical vibration. The device parts are brought to the implantation site in a pre-assembled configuration or are pre-assembled in the implantation site. In the pre-assembly specific ones of the device parts are still moveable relative to each other in a limited manner. The pre-assembled device parts are positioned relative to each other in a site-specific arrangement by moving the specific device parts relative to each other. The device parts are then locked in this site-specific configuration by being joined to each other with the aid of mechanical vibration, for which joining, adjacent and relative to each other moveable device parts are equipped with matched joining locations which face each other. Anchorage of the correspondingly equipped device parts takes place simultaneously with the joining or in a preliminary step. There may not be any anchorage of device parts in the bone tissue.

Aspect E: a plurality of device parts is brought to the implantation site in succession either along substantially the same path or along different paths and the device parts are joined to each other in the implantation site, joining being effected using mechanical vibration being applied to at least one of the device parts. Selected ones of the device parts may be equipped for being anchored in bone tissue with the aid of a liquefiable material and mechanical vibration. The device parts, which are equipped with matched pairs of first an second joining locations where they are to be joined, are positioned relative to each other in the implantation site with matched joining locations facing each other and are then joined to each other with the aid of mechanical vibration. Anchorage of the correspondingly equipped device parts takes place simultaneously with the joining or in a preliminary step. There may not be any anchorage of device parts in the bone tissue.

Suitable liquefiable materials for joining the parts of the device according to the invention are not biologically resorbable, whereas liquefiable materials for anchoring a part of the device in bone tissue may either be resorbable or non-resorbable.

Suitable non-resorbable liquefiable materials for first joining locations and possibly also for the anchorage of a device part are e.g.: polyolefines (e.g. polyethylene), polyacrylates, polymethacrylates, polycarbonates, polyamides, polyesters, polyurethanes, polysulfones, liquid-crystal-polymers (LCPs), polyacetals, halogenated polymers, in particular halogenated polyolefines, polyphenylene sulphones, polysulfones, Polyaryletherketones (E.g. polyetheretherketone PEEK, available under the trade name Victrex 450G or Peek Optima from Invibo) polyethers, or corresponding copolymers and mixed polymers or composites containing said polymers and fillers or reinforcing agents such as e.g. fibers, whiskers, nanoplatelets, or nanotubes. Particularly suitable are polyamide 11 or polyamide 12.

Suitable resorbable liquefiable materials for anchorage of a device part in bone tissue are e.g.: thermoplastic polymers based on lactic and/or gluconic acid (PLA, PLLA, PGA, PLGA etc) or polyhydroxy alkanoates (PHA), polycaprolactones (PCL), polysaccharides, polydioxanones (PD), polyanhydrides, polypeptides, trimethylcarbonates (TMC), or corresponding copolymers, or mixed polymers, or composites containing said polymers. Particularly suitable as resorbable liquefiable materials are: poly-LDL-lactide (e.g. available from Böhringer under the trade name Resomer LR708) or poly-DL-lactide (e.g. available from Böhringer under the trade name Resomer R208), as well as corresponding copolymers and mixed polymers or composites containing said polymers and fillers or reinforcing agents such as e.g. fibers, whiskers, nanoplatelets, or nanotubes.

The device according to the invention serves the same purposes as known implants and endoprostheses. The device serves in particular for fixing one viable tissue part to another viable tissue part, wherein the device according to the invention constitutes a fixing element, in particular a load bearing fixing element between the two tissue parts. The device may also serve for fixing an artificial element replacing a natural tissue part or an auxiliary element (e.g. auxiliary support part), wherein the device according to the invention constitutes the replacement part or auxiliary part as well as the fixing means.

The advantage of the device and the method according to the invention is the ease of the in situ assembly, the robustness of the assembly, the character of the assembly which makes it non-reversible under physiologic conditions and the easy and little limited in situ adaptability of the assembly.

For carrying out the method according to the invention a vibration device is used, e.g. an ultrasonic device comprising an ultrasonic transducer, a booster and a sonotrode or a sonotrode (vibrating tool) and an acoustic coupling piece (vibrating tool), wherein the sonotrode or the coupling piece is advantageously exchangeable. Preferably a set is provided which set comprises, in addition to device parts, vibrating tools with distal ends adapted to the contact locations of the device parts and proximal ends adapted to a fixation point of the vibration device or sonotrode respectively. The sets may further comprise printed or otherwise recorded instructions regarding implantation parameters such as e.g. vibration frequencies and application times suitable for the joining and possibly anchoring processes for implantation and assembly of the device parts of the set.

Exemplary embodiments of the method and the device according to the invention are described in further detail in connection with the following Figures, wherein:

FIGS. 8 to 14 show a first group of exemplary embodiments of aspect A of the invention, wherein a distal end of the based part is fixed within bone tissue via a base part, wherein the base part is anchored within an opening provided in the bone tissue, wherein the based part is fixed in or on the base part, and wherein the based part has varying functions;

FIGS. 15 and 16 show a second group of exemplary embodiments of aspect A of the invention, wherein this group is similar to the first group but wherein the base part is anchored in the marrow space of a suitably prepared tubular bone;

FIGS. 17 to 20 show a third group of exemplary embodiments of aspect A of the invention, for which the based part is joined to the proximal base part end which protrudes from an opening which is provided in the bone tissue and in which the base part is anchored;

FIGS. 25 to 32 illustrates a second group of embodiments of aspect B of the invention, wherein a based part is fixed relative to a bone surface with the aid of one or a plurality of base parts;

FIGS. 47 and 48 illustrate a second group of embodiments of aspect C of the invention wherein the base part is introduced through a further implant part to be joined to the based part;

FIGS. 49 to 54 show a first group of embodiments of aspect D of the invention, wherein a pre-assembled plurality of device parts is arranged in a site-specific configuration and the device parts are then joined to each other;

FIGS. 55 to 61 show a second group of embodiments of aspect D of the invention, wherein the device comprises, in addition to the plurality of pre-assembled or pre-assemblable device parts, a locking part for locking the pre-assembled device parts in the site-specific configuration;

FIGS. 1 to 7 illustrate exemplary embodiments of matched pairs of first and second joining locations suitable for the devices according to the invention and connections between such joining locations. The first joining location F comprises a liquefiable material and possibly energy directors E, the second joining location S comprises an undercut structure of a non-liquefiable material and possibly energy directors E. For joining the two matched joining locations, these are pressed against each other and mechanical vibration is coupled into one of the parts comprising either the first or second joining location from a side opposite the joining location. Pressure and vibration cause the liquefiable material in the region of the energy directors to liquefy and to penetrate in a liquid state into the structure of the second joining location and, on re-solidification, to form therewith a positive fit connection.

The main feature of joining two device parts comprising a matched pair of first and second joining locations using mechanical vibration is the fact that the liquefiable material of the first joining location is liquefied and penetrates in a liquid state into the structure of the second joining location which is usually undercut in the direction of the liquid flow. The resulting positive fit structures of the liquefiable material are characterized by forms which are dependent on the surface tension of the liquid state. The liquefiable material of these structures may adhere to the material of the second joining location but there is no necessity that it does.

Figure 1:
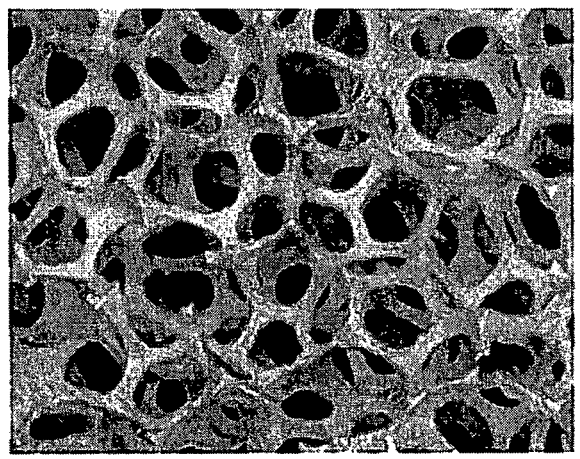
FIGS. 1 to 7 illustrate structures of second joining locations and joints achieved by joining matched pairs of joining locations.
Figure 2:
Figure 3:
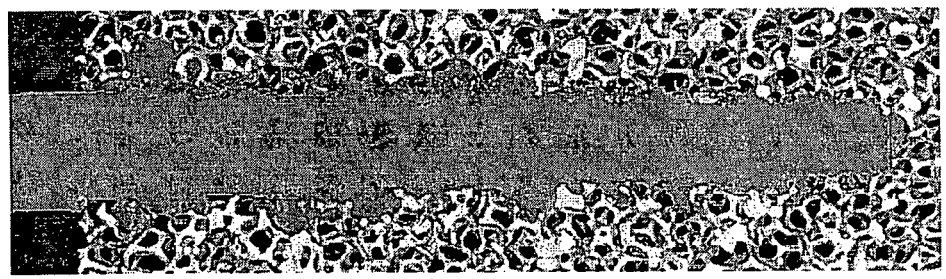

FIGS. 1 to 3 show as a first example of a second joining location S a foam structure e.g. consisting of a metal, e.g. titanium. FIG. 1 shows the foam structure before being penetrated by the liquefiable material, FIG. 3 shows a pin of the liquefiable material being anchored in the foam structure and FIG. 2 shows in a larger scale the interpenetration of the foam structure by the liquefiable material after re-solidification, i.e. the positive fit connection between the two. This positive fit connection which is visible in FIGS. 2 and 3 comprises in this first example structure elements of a size in the region of about 1 mm or less. A first joining location matched to the joining location as shown in FIGS. 1 to 3 comprises a liquefiable material, is adapted to the outer surface of the foam material (e.g. even) and is large enough to cover a plurality of the structure elements. The structure elements of the foam structure are able to act as a plurality of energy directors such that the first joining location does not need to be equipped with energy directors. However, the first joining location may also be constituted by a more or less pointed distal end of a pin-shaped device part, which pointed end acts as energy director.

Figure 4:
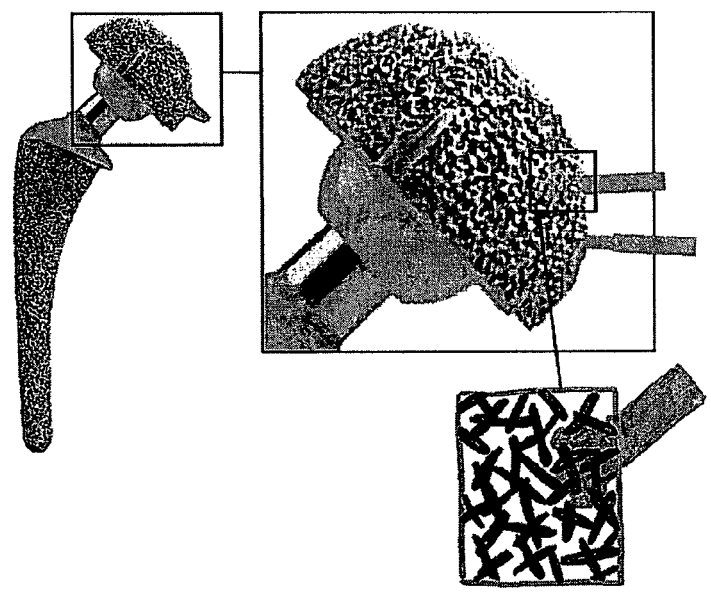

FIG. 4 shows in a cascade of three scales a second example of the second joining location and a positive fit connection between this second joining location and a first joining location. The illustrated second joining location is constituted by the surface of a hip joint prosthesis by S+G Implants GmbH, Lübeck, Germany. The surface structure of such implants consists of a metal (preferably titanium or a titanium alloy) and is e.g. produced by sintering a particulate material or by lost form molding. The structure elements have an average size from about 1 mm to about 2 mm. A first joining location matched to the second joining location according to FIG. 4 comprises a liquefiable material and is adapted to cover a plurality of the structure elements as discussed for the joining elements according to FIGS. 1 to 3. If the structure elements of the second joining location are more rounded than edgy, it is advantageous to equip the matched first joining location with energy directors.

Similar structures as shown in FIG. 4 being suitable for second joining locations may be made of trabecular metal by Zimmer, or of wire mesh as known from implants by Johnson & Johnson. Implants by Eska also have suitable surfaces.

Figure 5:
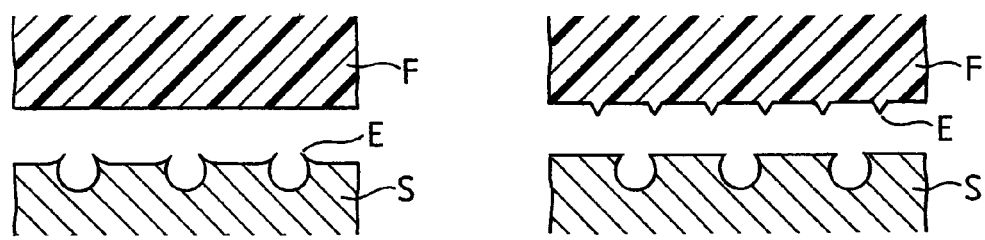

FIG. 5 illustrates second joining locations S comprising a more or less regular pattern of undercut openings (e.g. bores or grooves), which are manufactured or molded. In the second joining location S on the left, the mouths of the undercut openings protrude slightly from the overall surface and therewith are capable of acting as energy directors. A matched first joining location F may be completely even. The structure of the second joining location S on the left of FIG. 5 does not comprise energy directors and therefore energy directors E are advantageously provided on the first joining location. The second joining location structures according to FIG. 5 advantageously have a size of about 1 to several mm and the first joining location covers a plurality thereof.

Figure 6:
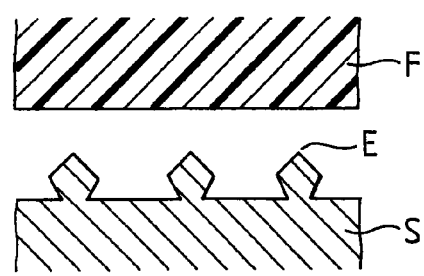

FIG. 6 shows a matched pair of joining locations F and S similar to the joining locations according to FIG. 5 wherein the second joining location structure comprises undercut protrusions (e.g. heads or combs with a narrower neck region) instead of openings. These protrusions, if equipped with more or less sharp edges or points act as energy directors also.

Figure 7:
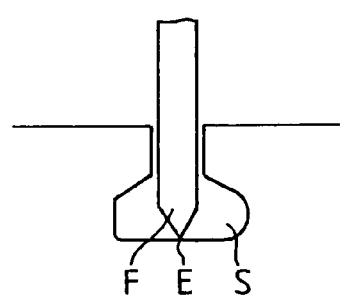

FIG. 7 shows a last example of a matched pair of joining locations, wherein the structure of the second joining location S, which is again an undercut opening, is larger than the first joining location F. The first joining location is situated at a distal end of a pin-shaped part, which pin-shaped part is introduced into the opening, when the parts to be joined are pressed against each other. The distal end of the pin is e.g. pointed for being capable of acting as energy director and the pin comprises enough of the liquefiable material for filling the undercut opening constituting the second joining location.

FIGS. 8 to 14 illustrate a first group of embodiments of aspect A of the invention and applications thereof. The device is an implant or an endoprosthesis and comprises a base part (first device part) and a based part (second device part), the based part being based in the bone tissue via the base part by being joined to the base part. The base part is adapted to fit into an opening to be provided in bone tissue and it is equipped for being anchored in this opening with the aid of a first liquefiable material and mechanical vibration. For this purpose it comprises the liquefiable material at least in surface areas to be in contact with the bone tissue or the liquefiable material is provided inside the base part and for the anchorage is pressed through openings to surfaces in contact with the bone tissue. The base part further comprises preferably on its proximal side one of the joining locations, preferably the first joining location. The based part comprises a distal end adapted to be joined to the base part and comprising one of the joining locations, preferably the second joining location.

FIG. 8 shows an anchor for e.g. anchoring a suture 21 or wire or other flexible device part relative to bone tissue. The anchor comprises a base part 1 (first device part) to be retained in an opening of bone tissue and a based part 2 (second device part), whose distal end is equipped for being retained in the base part 1 and whose proximal end is equipped for holding the suture or wire (further device part). The base part 1 is equipped for being anchored in hard tissue, in particular in bone tissue, with the aid of a liquefiable material and mechanical vibration and it comprises the first joining location 3. At least part of the outer surface of the base part 1 comprises a liquefiable material and possibly energy directors in form of ribs or other protrusions. The proximal surface of the base part is suitable for being contacted with a vibrating tool (contact location 4 for application of mechanical vibration for anchoring the base part in the bone tissue). The base part 1 further comprises an opening 5 extending from its proximal face towards the distal end, wherein the inner surface of the opening 5 comprises a liquefiable material and possibly energy directors (first joining location 3). The base part 1 consists e.g. entirely of the liquefiable material, e.g. of a thermoplastic polymer.

The based part 2 comprises, at its distal end, the second joining location 6 (e.g. according to any of FIGS. 1 to 6) and at its proximal end the contact location 7 for the application of the mechanical vibration for the joining process. The based part 2 is e.g. made of a suitable metallic material and its distal end is matched to the opening 5 of the base part 1. The second joining location 6 comprises e.g. undercut cavities and possibly energy directors (e.g. axial ribs).

For implanting and assembling the device comprising the base part 1, the based part 2 and possibly the suture 21 or wire, the base part 1 is e.g. positioned in a bore 10 provided in the bone tissue 11 and a vibrating tool 12 (vibrating tool for the anchoring process, e.g. sonotrode of an ultrasonic device) with a distal face being adapted to the proximal face (contact location 4) of the base part 1 is pressed against this proximal face. Caused by the action of vibration and pressure, the liquefiable material in contact with the bone tissue is liquefied and interpenetrates the porous structure of the bone tissue to form the desired anchorage of the base part 1 on re-solidification. Due to the high elasticity module of the base part material and due to the energy directors on its outer surface or on the bone surface, the base part material is only liquefied on this outer surface, the body of the base part keeping all its mechanical stability and strength such that the base part is able to function as a mechanically stable oscillator during the whole application of the mechanical vibration.

When the base part 1 is anchored in the bone tissue 11, at least the distal end of the based part 2 is introduced in the opening 5 of the base part and a further vibrating tool 15 (vibrating tool for the joining process) with a distal face being adapted to the contact location 7 of the based part 2 is applied to the based part. Application of mechanical vibration 1 liquefies the liquefiable material of the first joining location 3 in the opening 5 of the base part and makes it to fill the undercut cavities provided in the second joining location 6 to form a positive fit connection with the first joining location 3 of the base part and thereby joining the based part 2 to the base part 1.

The based part 2 may have various functions which are different from the function illustrated in FIG. 8 (suture or wire anchor), for which functions the proximal end of the based part is correspondingly adapted. Exemplary further functions of the based part 2 are fixation of soft or further hard tissue relative to the bone tissue, fixation of a rod, a rod clamp as used in spinal fusion or external fixation, of a supporting plate as used for osteosynthesis purposes or of another auxiliary device as for anchoring e.g. a tracker for navigation. For such fixation purposes the proximal end of the based part 2 may e.g. be equipped with an outer or inner thread. The base part 1 and the based part 2 together may also constitute a dental implant to which a further dental prosthesis part is to be fixed.

The main advantage of the two-part device according to FIG. 8 over a corresponding one-part implant being anchored in the bone tissue with the aid of a liquefiable material and mechanical vibration is the fact, that the based part has at least a limited adjustability when the base part is already definitively set in the bone tissue. Liquefaction of the material surrounding the opening 5, allows to force the based part into a desired position and orientation relative to the base part which may not exactly correspond with the original opening 5. Furthermore, a round or polygon form of the cross section of the opening 5 and the distal end of the based part 2 allows to select a desired one of a plurality of possible rotational positions of the based part relative to the base part. A further advantage of the embodiment according to FIG. 8 is the fact that both device parts can be made of one material only (no multi-material parts to be manufactured), wherein the high strength material needed for fixing a further device part is suitable also for the second joining location.

Device and method as illustrated in FIG. 8 may be altered in various ways, resulting e.g. in the following further embodiments:

- The base part comprises a core made of a non-liquefiable material, which core carries the liquefiable material for anchoring the base part in the bone tissue on its outer surface and which core comprises an opening constituting the second joining location (the core material being e.g. a sintered material presenting in the opening 5 a porous surface to be interpenetrated by the liquefiable material of the first joining location, pair of matched joining locations according to e.g. FIG. 4), and the based part comprises at least in the region of its distal end this liquefiable material constituting the first joining location (see also FIG. 9).
- The base part is made of a non-liquefiable material and comprises passages connecting the opening 5 with the outer surface and a liquefiable material is provided in the opening 5. For anchoring the base part in the bone tissue, mechanical vibration and pressure are applied to the liquefiable material in the opening 5 for pressing it partly through the passages and into the bone tissue, the liquefiable material remaining in the opening 5 constituting the first joining location (see FIG. 11).
- The base part consists entirely of a non-liquefiable material and is fixed in the bone tissue e.g. by comprising a thread and by being screwed into the bone tissue. The base part is equipped with the second joining location (e.g. according to FIG. 7) and the based part is equipped with the first joining location.
- Instead of an opening 5, the base part comprises a proximal protrusion corresponding to an opening in the based part where the joining locations are provided (see FIG. 14).

FIG. 9 shows a further exemplary embodiment of aspect A of the invention. The device is suitable for being implanted and assembled with the method as shown in FIG. 1. The base part 1 comprises a core 22 of a non-liquefiable material, which core 22 carries on its outer surface the liquefiable material for anchoring the base part 1 in the bone tissue, and it further comprises an opening 5 extending from the proximal face towards the distal end of the base part and constituting the second joining location (according to FIG. 7). This opening 5 is a bore with an enlarged bottom region serving as undercut cavity for the positive fit connection with the based part 2 but also for snapping the based part in before the joining process.

Two versions 2.1 and 2.2 of the based part are shown, wherein both versions consist of the liquefiable material and comprise a distal end being equipped for being snapped into the enlarged bottom region of the opening 5. Version 2.1 of the based part comprises a groove 25 running across its distal face and possibly carrying on along the lateral surface of the based part to its proximal face. The groove 25 is shaped to be capable of guiding a suture 21, such that when the based part 2 is snapped into the base part 1, the suture 21 can be moved along the groove e.g. for being tightened. On joining the based part 2.1 to the base part 1, the material around the groove 25 is liquefied and on re-solidification the based part 2 is joined to the base part and at the same time the suture 21 is fixed in the groove 25.

Version 2.2 of the based part comprises a suture 21 being fixed to it, e.g. by being positioned in the mold in which the based part is produced by injection molding. For enabling adjustment of the position of the suture 21 relative to the anchored base part 1, the based part 2.1 or 2.2 has e.g. a round cross section and can be rotated in the opening 5 when being snapped into the latter.

FIG. 10 shows a further exemplary embodiment of aspect A of the invention. The illustrated device again serves as a suture anchor and again comprises a base part 1 and a based part 2 and is implanted according to the method as shown in FIG. 8. Based part 2 and base part 1 are adapted to each other such that the based part 2 can be snapped into the opening 5 of the base part 1 in at least two different depths. A first end of the suture 21 is e.g. fixed in the based part 2 and a second end of the suture 21 is threaded e.g. through soft tissue 27 and then through bores 28 and 29 leading through base part 1 and based part 2 and being aligned to each other when the based part is clicked into the base part in its outermost clicking position. When the second suture end is fixed in any suitable position, the suture tension can be increased by pressing the based part 2 into a deeper snap position. The based part 2 together with the suture 21 is then fixed in the base part by applying the mechanical vibration to the proximal face of the based part 2.

Figure 11:
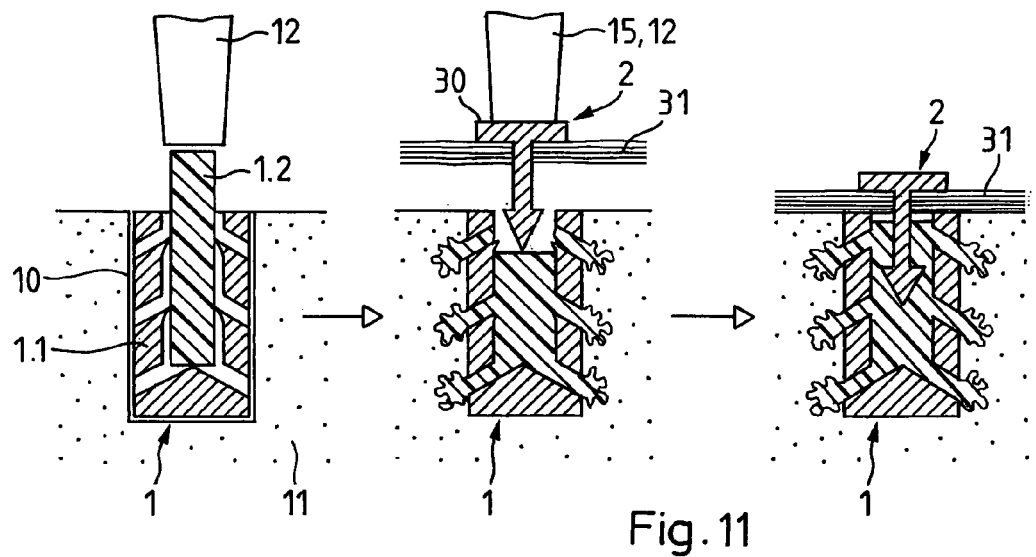

FIG. 11 shows a further application of a device according to aspect A of the invention. The device serves e.g. for fixing soft tissue (e.g. ligament or tendon 31) relative to the bone tissue 11 in which the based part 2 is fixed via the base part 1.

The base part 1 comprises a perforated sleeve 1.1 comprising on its inside surface energy directors and consisting of a non liquefiable material and an insert 1.2 of a liquefiable material which is positioned in the sleeve 1.1. The sleeve is positioned in an opening 10 which is provided in the bone tissue 11 and is pressed into the sleeve and vibrated by a first vibrating tool 12 positioned against the proximal face of the insert 1.2. The insert material is thereby liquefied and pressed through the sleeve perforations into the bone tissue 11 of the wall of opening 10 such anchoring the base part 1 in the bone tissue. The rest of the insert in the sleeve constitutes the first joining location.

The based part 2 consists of a non-liquefiable material and comprises a head 30 for being retained in a tendon or ligament 31 through which the distal end of the based part 2 is pushed before it is joined to the base part. The distal end of the based part constitutes the second joining location by comprising a head which is preferably pointed (energy director). For joining the based part to the base part, a further vibrating tool 15 or the same one (12) as for anchoring is positioned against the head 30.

Figure 12:
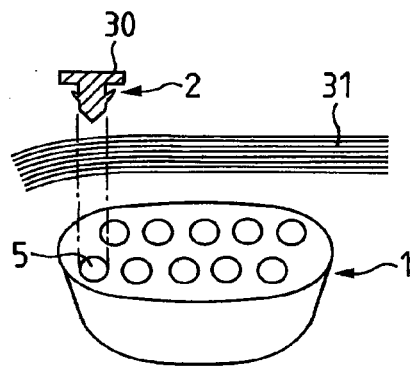

FIG. 12 shows very schematically a further device according to aspect A of the invention, which device is applicable for fixing e.g. a ligament or tendon 31 to bone tissue. The device is equipped similar to the devices as illustrated in FIG. 8, 9 or 11. Other than shown in the named Figs. though, the base part 1 of the device according to FIG. 12 is capable to accommodate more than one based part 2 of which only one is illustrated. The base part 1 may have any suitable form, e.g. substantially round or substantially rectangular. The based part 2 shown in FIG. 12 comprises barbs which are able to preliminarily retain the based part 2 in the corresponding opening 5. It is advantageous to first position and preliminarily retain all based parts 2 in their corresponding openings 5 in the anchored base part 1 and only then to finally join all based parts 2 to the base part 1 with the aid of the mechanical vibration being applied to the head 30 of each one of the based parts. The barbs may also constitute the structure of the second joining location (second joining location according to FIG. 6).

Figure 13:
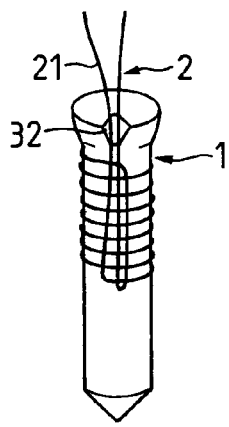

FIG. 13 shows a device according to aspect A of the invention, in which the based part 2 is a suture 21 and which enables anchorage of the substantially pin-shaped base part 1 and joining of base part 1 and suture 21 (based part 2) simultaneously. The base part e.g. consists of the liquefiable material and the regions in which it is anchored in the bone tissue are substantially the same as the first joining locations, namely the lateral surfaces of the base part. The suture 21 consists of a non-liquefiable material. It is wound and possibly knotted round the base part 1 for which a groove may be provided on the base part, in particular for passing the suture from the lateral sides of the base part to the proximal face thereof (groove 32). The base part 1 and the suture (based part 2) are together introduced into a corresponding opening provided in the bone tissue and the mechanical vibration is applied to the proximal end of the base part, whereby the base part 1 is anchored in the bone tissue on its distal and lateral sides and at the same time the suture 21 is joined to the base part 1.

Figure 14:
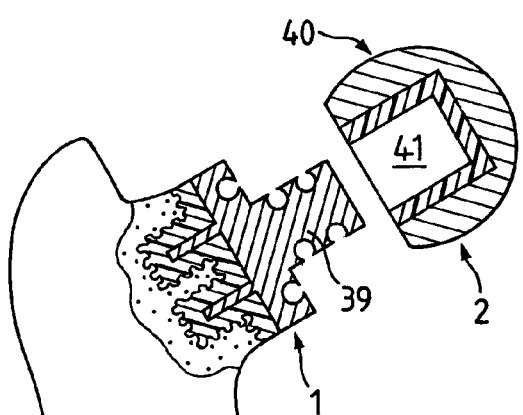

FIG. 14 illustrates a further application of a two part device to be implanted e.g. according to the method as illustrated in FIG. 8. The application concerns resurfacing of a bone or cartilage surface constituting a bearing surface in a joint. FIG. 14 illustrates resurfacing of a femoral head, the application may however in the same manner concern a cup-like structure. Such resurfacing implants replace primarily the destroyed cartilage layer but try to spear most of the underlying bone structure. Comparable approaches can be used for almost all joints in the human skeleton, being convex, concave, flat or of a multi-curvature geometry.

FIG. 14 also illustrates an embodiment of aspect A of the invention in which the base part 1 does not comprise an opening for the distal end of the based part 2, but in which the base part 1 comprises a protrusion 39 and the based part 2 comprises an opening 41 adapted to the protrusion (also possible: opening on base part and protrusion on based part). This principle is adaptable as a variant to other embodiments of aspect A of the invention as described above. Furthermore, FIG. 14 illustrates a base part 1 which is not anchored in one opening provided in the bone tissue but in a plurality of such openings, which plurality of openings may be rather small (e.g. two as illustrated) or very large, i.e. being constituted by a natural or manufactured roughness of a bone surface (e.g. surface of cancellous bone). As mentioned for the feature of the base part comprising a protrusion adapted to a based part opening, the feature of the plurality of openings provided in the bone tissue for anchorage of the base part is adaptable to other ones of the above described embodiments of aspect A of the invention.

In the device according to FIG. 14, the base part 1 is anchored in a plurality of openings of the correspondingly prepared femoral bone. The base part 1 comprises a plurality of distal projections which comprise the liquefiable material and which reach into the bone openings and are anchored therein with the aid of the liquefiable material and mechanical vibration. The proximal side of the base part is e.g. made of a metal, ceramic, or non-liquefiable polymer material and comprises a proximal protrusion 39 comprising a surface structure with undercut cavities (second joining location). The based part 2 comprises the bearing surface (40) replacement and opposite the bearing surface an opening 41 wherein the liquefiable material of the first joining location is situated.

FIGS. 15 and 16 illustrate a second group of exemplary embodiments of aspect A of the invention. These embodiments differ from the above described embodiments of a first group in that the opening in the bone tissue in which the base part 1 of the device is anchored is not an opening which is made in the bone tissue but is the marrow space of a tubular bone 45. The device is e.g. an endoprosthesis replacing a joint part.

FIG. 15 illustrates a substantially hollow base part 1 made e.g. of the liquefiable material (also possible: comprising core of non-liquefiable material coated at least partly with the liquefiable material) and designed for being anchored not only on the inside bone surface of the tubular bone 45 but also on its face created by removing the one end section of the tubular bone 45 which is to be replaced by the device. The bone section to be replaced is e.g. part of a smaller joint (e.g. finger joint). The proximal end of the based part 2 represents most of the replacement and the distal end is designed for fitting into the base part 1 and for constituting the second joining location (e.g. according to any one of FIG. 1 to 3, 4, 5 or 6).

FIG. 16 illustrates a device according to aspect A of the invention being a hip joint prosthesis, wherein the base part 1 constitutes the shaft of the prosthesis to be anchored in the femoral bone and the based part 2 is an intermediate prosthesis part, to which a further based part 2' (based on the based part 2 which is itself based on the base part 1, and constituting the ball section of the prosthesis). The joining locations between base part 1 and based part 2 and between based part 2 and further based part 2' are shown without detail. However, each matched pair of joining locations comprises a first and a second joining location and is equipped to result after application of mechanical vibration in a positive fit connection between a corresponding surface structure of the non-liquefiable material of the second joining location and the liquefiable material of the first joining location having in a liquid state penetrated the named surface structure. Advantageous second joining locations for the device according to FIG. 16 are in particular structures as shown in FIG. 4, however structures according to FIG. 1 to 3 or 5 or 6 are also applicable.

It is possible also that all three or at least two of the parts 1, 2 and 2' of the prosthesis according to FIG. 16 are joined immediately before implantation, i.e. by the surgeon and within the sterile space and that the assembled prosthesis is anchored as one part in the marrow space of the femoral bone.

Figure 19:
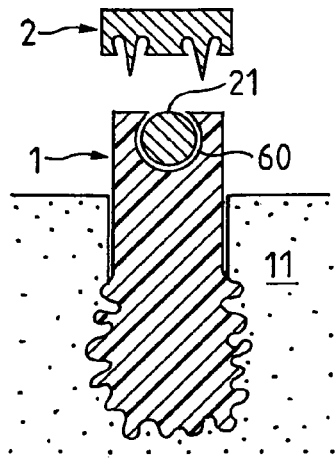
Figure 20:
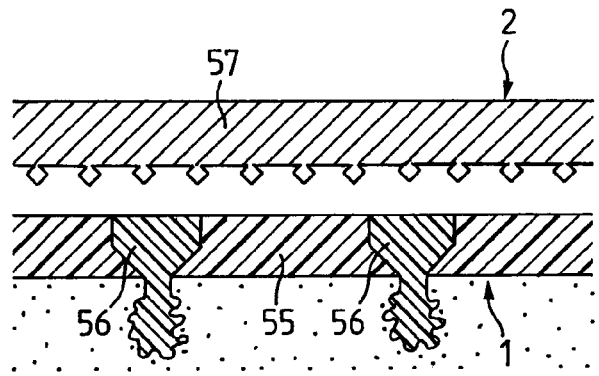

FIGS. 17 to 20 show embodiments of a third group of exemplary embodiments of aspect A of the invention. In this group of embodiments the based part 2 is joined to the proximal end of at least one base part 1, wherein this proximal end protrudes from the opening in the bone tissue in which the base part 1 is anchored and wherein the assemblage of base part 1 and based part 2 serves for securing a further tissue (e.g. soft tissue) or a further device part and wherein the further tissue or device part is fixed relative to the bone tissue in which the base part 1 is anchored by the assemblage of the base part proximal end and based part 2. Instead of the named fixing function, the based part may also serve for strengthening or stiffening the base part (FIG. 20).

FIG. 17 shows a device and a corresponding implantation method according to aspect A of the invention which serve for fixing a soft tissue part (e.g. tendon or ligament 31) or a further device part (e.g. supporting plate as used for osteosynthesis purposes) relative to bone. The base part 1 is e.g. pin-shaped and consists of the liquefiable material. It is anchored in an opening 10 in bone tissue 11 with the aid of the liquefiable material and mechanical vibration, such that its proximal end, which is e.g. pointed, protrudes from the opening 10. The tendon or ligament 31 is then pushed against the proximal end of the base part 1 such that this proximal end penetrates through the ligament or tendon 31 which is either pre-perforated or not. The based part 2, which is formed as a sort of head for the base part 1 and, on its distal side, comprises the second joining location (preferably according to FIG. 7, pointed distal end of base part serving as energy director), is then positioned on and joined to the proximal end of the base part 1 by applying mechanical vibration to the head-shaped based part 2. As shown in FIG. 17 an outer rim of the head-shaped based part 2 may comprise distally protruding sharp edges which, on joining the based part 2 to the base part 1, are pressed into the tendon or ligament 31 and serve as further means for retaining the tendon or ligament 31 relative to the bone tissue 11 in which the base part 1 is anchored.

FIG. 18 shows the same method and similar device parts as FIG. 16 used for securing an intervertebral element 50 (further device part), e.g. an intervertebral fusion element or cage, serving for fixing two neighboring vertebral bodies relative to each other and to be secured between the two neighboring vertebral bodies 51. The positioned intervertebral element 50 is shown from a lateral side. It is positioned between the vertebral bodies 51 and then two or more than two pin-shaped base parts 1 are anchored in the vertebral bodies above and below the intervertebral element 50. A substantially bar- or plate-shaped based part 2 is then joined to the proximal base part ends and moved towards the intervertebral element 50 to form together with the base parts 1 a clasp which lies against the face of the intervertebral element 50 and secures it in its position between the vertebral bodies 51.

FIG. 19 shows a pin-shaped base part 1 which is anchored in bone tissue 11 and comprises a proximal end projecting from the bone tissue and comprises a groove 60 into which e.g. a suture 21 (or wire or rod) can be snapped or positioned and in which the suture 21 can then be secured by joining the based part 2 to the proximal end of the base part 1 (matched pair of joining locations e.g. according to FIG. 5)

FIG. 20 illustrates a further embodiment of aspect A of the invention, in which the base part 1 is an assembly of a base plate 55 which is secured to the surface of a bone by anchors 56 in the bone tissue extending through openings in the base plate 55 or being fixed to the base plate side facing the bone surface. The base plate is preferably thin and in particular flexible in all directions. The based part 2 is a plurality of stiffening elements 57 to be joined to the one side of base plate 55 facing away from the bone surface (proximal side). Either the base plate 55 or the stiffening elements 57 comprise the first joining location (e.g. the base plate 55), the other one the second joining location (e.g. the stiffening elements 57), which is e.g. structured according to FIG. 6 but may also be structured according to any one of Fogs 1 to 3, 4 or 5.

The flexible base plate is implanted e.g. across a bone fracture and flexibly adapted to the form of the corresponding bone surface. The implanted base plate is then stiffened preferably only locally depending on the required stabilization of the fracture by correspondingly formed and positioned stiffening elements 57 (e.g. parallel stiffening stripes distanced from each other, crosswise arranged stiffening stripes or stiffening plates). Advantageously the stiffening elements are flexible also and only the combination of base plate and stiffening element has the stiffness required for stabilizing the fracture. It may furthermore be advantageous to make the base plate from a resorbable material such that stabilizing needs to be taken over gradually by the bone in which the fracture is healing (prevention of stress shielding).

Another or an additional advantage which can be achieved with an assembly as shown in FIG. 20 is the fact that the pins 56 and the openings provided therefore in the base plate 55 can be covered with the stiffening elements 57. This is particularly advantageous if the assembly serves for replacing a bearing surface of a joint, e.g. of a joint socket and one plate is used as stiffening element.

It is obvious for one skilled in the art to combine features of the above described and illustrated embodiments of aspect A of the invention in different ways and therewith to create further embodiments which are still encompassed by the invention.

FIGS. 21 to 24 illustrate a first group of embodiments of aspect B of the invention. These embodiments encompass a device comprising a based part 2 and at least one base part 1 and a method for implanting the device in an opening provided in bone tissue by first positioning at least a distal end of the based part in the opening and then pushing the base part or the base parts between the bone tissue and the base part and thereby anchoring the base part in the bone tissue of the wall of the opening and simultaneously joining it to the based part. The base part preferably consists of a liquefiable material and comprises the first joining location, which joining location is situated at a lateral side of the base part. The based part comprises preferably the second joining location, which is situated at a lateral side of the based part. The base part may also comprise a core of a non-liquefiable material and be coated on one lateral side with the liquefiable material, wherein the opposite lateral side then constitutes the second joining location, the first joining location being arranged on the base part.

Figure 21:
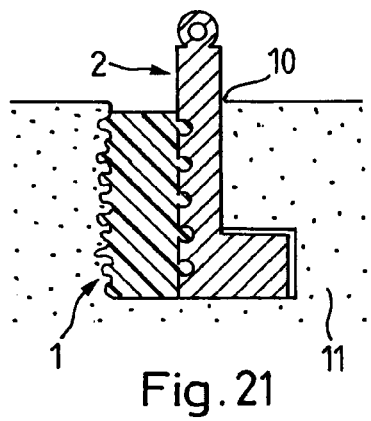
FIGS. 21 to 24 show a first group of exemplary embodiments of aspect B of the invention, wherein a based part is positioned in an opening in bone tissue with the aid of one or a plurality of base parts being pushed into the opening beside the based part.

FIG. 21 shows a device according to aspect B of the invention, the device being a suture anchor. The device comprises a based part 2 and a base part 1 which are implanted in an opening 10 provided in bone tissue 11. The base part 1 consists of the liquefiable material and on a lateral side comprises the first joining location. The based part 2 is e.g. equipped with an eyelet (positioned e.g. on its proximal end) for fixing a suture or wire consists of a non-liquefiable material and comprises on its lateral side the second joining location (e.g., as illustrated in any one of FIG. 1 to 3 or 4, 5, or 6). For implanting the device, the based part 2 is first positioned in the opening 10 provided in the bone tissue 11. The base part 1 is then pushed into the opening beside the based part 2 on the one side thereof which comprises the second joining location. This pushing is accomplished with the aid of a vibrating tool (not shown) which is applied to the proximal face of the base part 1. Simultaneously with the pushing, mechanical vibration is coupled from the tool into the base part. Due to the pushing motion the matched pairs of first and second joining locations are brought into contact with each other and due to the mechanical vibration the base part 1 is anchored on its one lateral side in the bone tissue of the wall of opening 10 and simultaneously joined on its other, opposite lateral side to the based part 2. This results in the based part 2 being laterally fixed relative to the bone tissue via the base part 1 and, in particular if the base part has the shape of a wedge, also in the based part being pressed against the bone wall of the opening 10 on the side opposite the base part.

In the embodiment illustrated in FIG. 21, the opening comprises an undercut region at least on its one side and the based part 2 comprises a foot which fits into the undercut region. This design of opening 10 and based part 2 serves as an additional means for retaining the based part 2 in the opening 10 but requires a correspondingly larger entrance to the opening, which is then filled by the base part 1.

Figure 22:
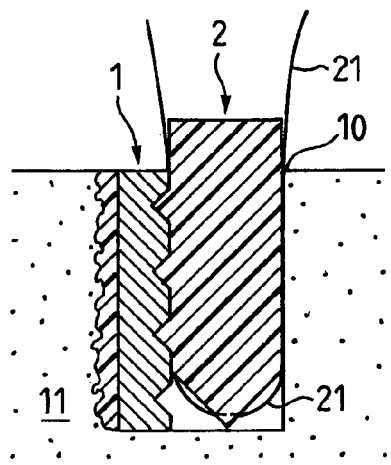

FIG. 22 shows a further embodiment of aspect B of the invention, wherein the implanted device serves again as a suture anchor and makes it possible to fix the suture 21 relative to the bone tissue 11 simultaneously with retaining the based part 2 with the aid of base part 1. Again, for implantation, the base part 1 is introduced in the opening 10 provided in the bone tissue 11 and the base part 1 is then pushed between the opening wall and the based part. Other than shown in FIG. 21, according to FIG. 22 the base part 1 comprises the second joining location on a side opposite its being anchored in the bone tissue and the base part 2 comprises the first joining location, wherein the suture 21 extends across this first joining location and on liquefaction of the liquefiable material of this first joining location is immersed in this material to be retained therein when it re-solidifies.

Figure 23:
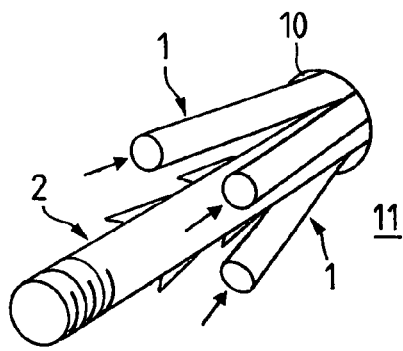
Figure 24:
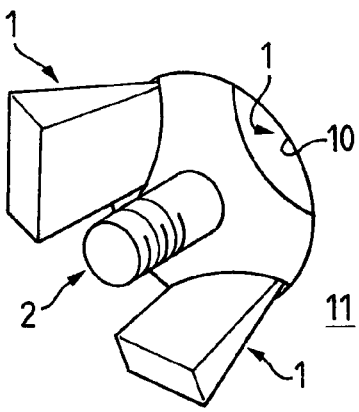

FIGS. 23 and 24 show embodiments of aspect B of the invention in which more than one base part 1 is used for fixing the based part 2 relative to the bone tissue 11 of which a surface is visible. In both cases the proximal end of the based part 2 is shown to be equipped with a thread which is used for fixing a further device part to the based part. The opening 10 in the bone tissue 11 which is provided for the implantation can in both cases be a bore with a round cross section wherein for the embodiment shown in FIG. 23, the bore is lightly larger than a corresponding cross section of the based part 2, and for the embodiment as shown in FIG. 24 the bore has a same cross section as an outer cross section of the based part, wherein this outer cross section encompasses concave portions to which the shape of the base parts 1 is adapted.

FIGS. 25 to 32 show a second group of embodiments of aspect B of the invention, wherein the based part is positioned relative to a bone surface and the base part is pushed between the based part and the bone surface for being simultaneously anchored in the bone surface and joined to the based part.

Figure 25:
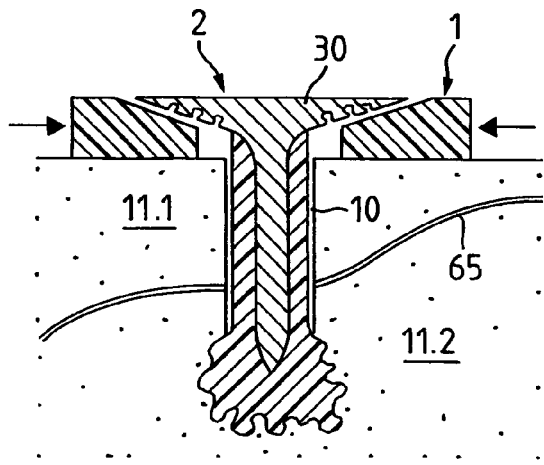

FIG. 25 shows as a device according to the invention a based part 2 whose distal end is equipped for being anchored in an opening in bone tissue with the aid of a liquefiable material and mechanical vibration. The opening 10 provided for the based part reaches e.g. across a bone fracture 65 from a first bone fragment 11.1 into a second bone fragment 11.2, wherein the based part 2 is dimensioned to be only anchored in the second bone fragment 11.2. The based part 2 further comprises a proximal head section 30 with a cross section larger than the cross section of opening 10. The head section 30 and a core of the based part 2 are preferably made of a non-liquefiable material and the head preferably comprises a slanting under side which is equipped with a surface structure suitable as second joining location (e.g. according to any of FIG. 1 to 3 or 4, 5, or 6. The based part 2 is anchored in opening 10 and then at least one wedge-shaped base part 1 is pushed between the bone surface of the first bone fragment 11.1 and the head section of based part 2. Simultaneously the based part is vibrated by a vibrating tool applied to its proximal face. During such pushing and vibration, the base part 1 is not only on the one side joined to the head section 30 of the based part 2 and on the other side anchored in the bone tissue but also the two bone fragments separated by the fracture are pulled against each other. The bone surface in which the base part 1 is to be anchored may for such anchorage have been provided with a rough surface.

FIGS. 26 to 31 show further embodiments of aspect B of the invention, according to which aspect at least one base 1 part is pushed between a bone surface and a based part 2 while being vibrated such that the base part is simultaneously anchored in the bone tissue and joined to the based part thereby fixing the based part relative to the bone tissue. All FIGS. 26 to 31 show applications concerning intervertebral implants replacement, wherein the intervertebral element (based part 2) and the base part or base parts are implanted e.g. from the frontal side or from a lateral side of the vertebral column.

Figure 26:
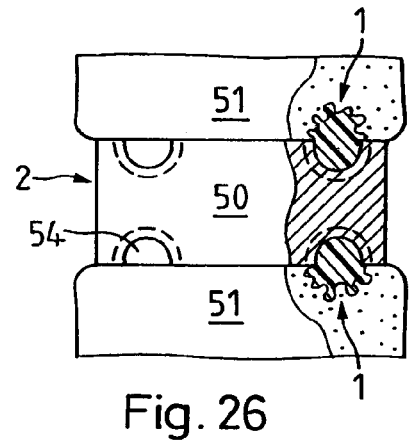
Figure 27:
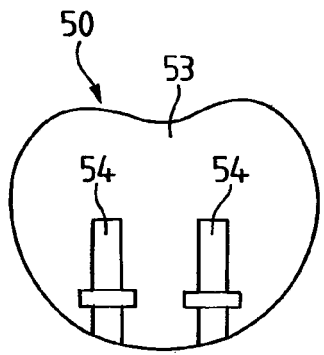

FIGS. 26 and 27 show an intervertebral element 50 (fusion element, e.g. cage) replacing a natural intervertebral disc and constituting the based part 2 of a device according to aspect B of the invention. The intervertebral element 50 is shown positioned between two neighboring vertebral bodies 51 (FIG. 26, left: before placement of the base parts; right: after placement of the base parts) and viewed from above (FIG. 27). The intervertebral element 50 is secured relative to the two vertebral bodies 51 with the aid of e.g. two upper and two lower base parts 1 which are e.g. pin-shaped and comprise the liquefiable material for being able to be anchored in the bone tissue of the vertebral bodies and constituting the first joining location. The base parts e.g. consist fully of the liquefiable material or comprise a core of a non-liquefiable material which is at least partly coated with the liquefiable material. In the latter case the core preferably protrudes at the distal end of the base part and there comprises a sharp point or self reaming edges.

The base parts are pushed between the vertebral body 51 and the intervertebral element 50 and are simultaneously vibrated by applying a vibrating tool to their proximal face. For allowing such pushing in of the base parts 1 the outer cortical bone layer of the relevant regions of the frontal or lateral side of the vertebral bodies 51 is removed and the intervertebral element 50 comprises on its upper and lower face 53 corresponding channels 54 with a ring shaped extension or other undercut structures (second joining location, visible in FIG. 27). On pushing and vibrating the base part 1 between the vertebral body 51 and the intervertebral element 50 the liquefiable material of the base part 1 is liquefied and forced into the bone tissue of the vertebral body 51 on the one side and into the ringshaped extension or other undercut structures of the channel in the intervertebral element 50. This is illustrated on the right hand side of FIG. 26.

Figure 28:
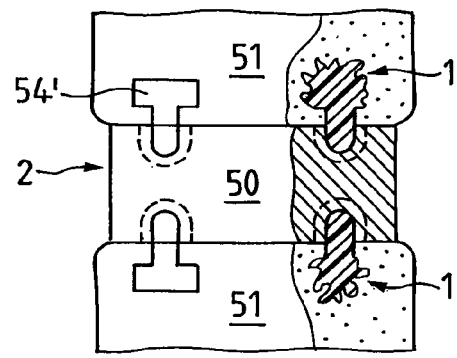
Figure 29:
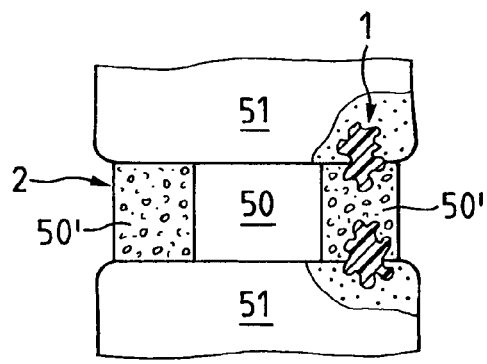

FIGS. 28 and 29 show the same application as FIGS. 26 and 27 (same view as in FIG. 26). According to FIG. 28 the vertebral bodies 51 are shown to also comprise channels 54' for introduction of the base parts 1. The channels advantageously have an undercut cross section and the base parts have cross sections adapted to the undercut channel. According to FIG. 29 the intervertebral element 50 is equipped with regions 50' of a porous material (e.g. a metal foam material) which can be penetrated by the base parts 1 like the cancellous bone of the vertebral body 51 (see also FIG. 3). Therefore, it may not be necessary to provide channels 45 in the intervertebral element 50.

FIG. 30 shows a further exemplified embodiment of aspect B of the invention and illustrates a further application of device and method regarding intervertebral disc replacement. The intervertebral element 50 (based part 2) has the form of a known intervertebral disc implant (non fusion element) and, in the present embodiment, comprises not only a disc element 70 but also an upper and a lower retaining element 71 for keeping the disc element 70 in place and to be fixed to the end plates of the vertebral bodies 51. The top of FIG. 30 shows part of the lower retaining element 71 and one of the base parts 1 in a lateral section of the vertebral column before introduction of the base part 1, and below the assembled and implanted device in a section from the front side to the dorsal side. The retaining elements 71 comprise back and front rims 72 protruding against the vertebral body 51 such that when the retaining element 71 is positioned on the vertebral body, there is a laterally open gap 73 between the endplate of the vertebral body 51 and the retaining element 71, into which gap the base part 1 is to be pushed. The one side of the retaining element 71 facing away from the disc element 70 is further equipped with a pattern of e.g. undercut cavities for being able to function as second joining location (not shown). The base part 1 comprises a core of a non-liquefiable material and is partly coated with the liquefiable material, constituting the means for anchoring and the first joining location 6. Its distal end of the non-liquefiable material is preferably equipped with self-reaming structures 74. The base part may in this case also comprise a perforated sleeve with the liquefiable material positioned therein, wherein the distal end of the perforated sleeve comprises the self-reaming structures (similar to FIG. 32).

The intervertebral element 50 including the disc element and the retaining elements 71 (based part 2) is positioned between two neighboring vertebral bodies 51. Then upper and lower base parts 1 are introduced between the retaining parts 71 and the vertebral body 51, i.e. into gaps 73, while the base part 1 is vibrated by application of a vibrating tool to the proximal end of it. Introduction and simultaneous self reaming, joining to the intervertebral element and anchorage in the bone tissue of the vertebral body are thereby effected.

Preferably the vibrating tool used for pressing and vibrating the base part 1 is designed for being able to hold one base part 1 such that it can be used not only for application of mechanical vibration and pressure to the base part but also for positioning it in the first place.

FIG. 31 shows a further exemplary embodiment of aspect B of the invention in an application regarding vertebral disc replacement (fusion element). The device again comprises an intervertebral element 50 (based part 2) and a plurality of base parts 1 designed for securing the based part 2 relative to the bone tissue of two neighboring vertebral bodies 51. The intervertebral element 50 is e.g. a cage-like structure of a non-liquefiable material which is filled with bone fragments or with a bone replacement material. The openings of the cage structure and the bone fragments or bone replacement material constitute the second joining locations. The base parts 1 are staple-shaped and are e.g. made of the liquefiable material, wherein the two distal ends of the base part 1 are pushed between the intervertebral element 50 and the bone tissue of the vertebral body 51 and constitute on the one side the first joining location and on the other side the means for anchorage in the bone structure of the vertebral endplates. Advantageously, the staple-shaped base part 1 has a further protruding area in its center, which is anchored in the intervertebral element on pushing the base part 1 against the intervertebral element 50. The based part may also comprise a core of a non-liquefiable material which is at least partly coated with the liquefiable material.

FIG. 31 shows the two vertebral bodies 51 and the intervertebral element 50 therebetween from the front side. The base part 1 on the right hand side is positioned for application of mechanical vibration and pressure using a vibrating tool 12 (sonotrode). The base part 1 on the left hand side is joined to the intervertebral element 50 and is anchored in the vertebral end plates.

FIG. 32 shows a further embodiment of aspect B of the invention, wherein the device is to be fixed relative to a bone surface using a base part which is pushed between the bone surface and a based part of the device. The base part 1 of this embodiment comprises a wedge shaped sleeve comprising an inside channel 80 and openings connecting the channel 80 with the outside surface of the sleeve (perforated sleeve). The sleeve may further comprise self-reaming teeth on the one side which is to be anchored in the bone tissue. The liquefiable material is positioned inside the channel 80. The bone surface may be the inside surface of a tubular bone and the based part 2 may be a shaft of an endoprosthesis to be fixed in the marrow space of this tubular bone. Implant and bone are shown only partly in FIG. 32.

For implantation, the base part 2 according to FIG. 32 is positioned in the tubular bone and preliminarily retained by positioning the wedge-shaped base part 1, which is possibly pushed whereby the self-reaming teeth are worked into the bone tissue. The base part 1 is then pressed further into the marrow space by applying a vibrating tool 12 to the proximal surface of the liquefiable material which due to the pressure and vibration is at least partly liquefied and pressed through the openings to anchor the implant on the one side in the bone surface and on the other side in the structure of the second joining location (e.g. according to FIG. 5) of the based part on the other side. FIG. 32 shows the preliminarily positioned wedge-shaped base part 1 on the left side and the same device after application of pressure and vibration on the right side.

The base part 1 according to FIG. 32 may comprise openings from the central channel to the surface of the sleeve only on its side facing the based part 2 and being anchored in the bone surface with barbs or solely with the aid of the self-reaming teeth or other suitable structures such as e.g. barbs.

Figure 33:
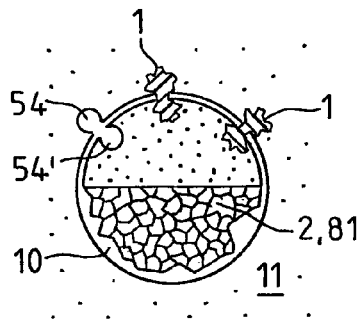
FIGS. 33 to 35 show a third group of embodiments of aspect B of the invention, wherein the based part to be fixed relative to bone tissue is a bone tissue part.
Figure 34:
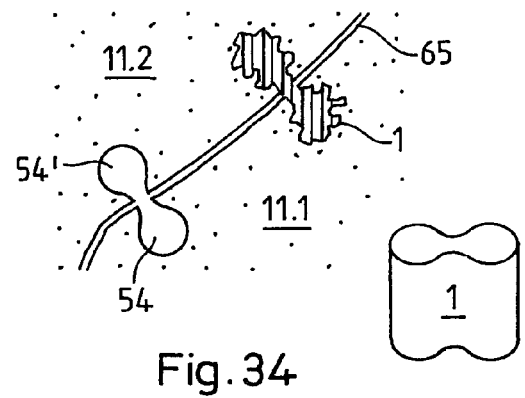
Figure 35:
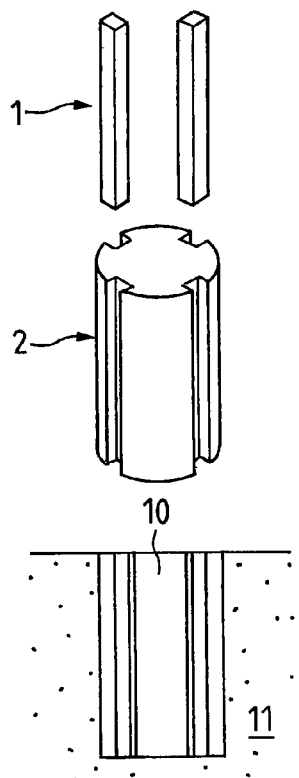

FIGS. 33 to 35 illustrate a third group of embodiments of aspect B of the invention which embodiments are similar to the first group embodiments but for which the based part 2 is a further bone tissue part or consists of a bone replacement material.

FIG. 33 shows a bone-tendon graft 81 (based part 2) positioned in a tunnel or bore 10 in bone tissue 11 and fixed within the tunnel or bore via base parts 1 which are pushed between the bone part of the bone region of the graft 81 and the bone of the tunnel or bore wall. Therein channels 54 and or 54' may be provided in either bone tissue. Depending on the bone tissues to be joined via the base parts 1, it may be possible to push the base parts 1 therebetween without the need of channels 54 and/or 54'. It is further possible to equip the base parts as earlier shown with a core of a non-liquefiable material and self-reaming structures e.g. on a distal end thereof (as e.g. shown in FIG. 30). In such a case the base elements will provide channels and it is not necessary to provide them beforehand.

FIG. 34 shows a similar application of aspect B of the invention in which a bone fragment 11.1 on one side of a bone fracture 65 is fixed to a bone fragment 11.2 on the other side of the fracture via a base part 1 or a plurality thereof (in the language as used before: one bone fragment representing the based part 2 which is joined to the base part 1 and the other bone fragment representing the bone tissue 11 in which the base part is anchored). Channels 54 and 54' in the bone fragments have preferably an undercut cross section and the base parts 1 have a corresponding cross section. Such base part 1 is shown on the right hand side of FIG. 34.

FIG. 35 shows a further embodiment of aspect B of the invention, wherein a based part 2 of bone tissue is fixed in an opening 10 in bone tissue 11 with the aid of a plurality of base parts 1 which are pushed between the based part 2 and the wall of opening 10. Therein the based part 2 may consist of autologous or homologous bone tissue or of a bone replacement material and constitute a plug to fill an opening caused by harvesting bone tissue. On the other hand the bone material 11 may constitute an implant made of a bone replacement material and the plug may be made of autologous bone tissue and serve for promoting ingrowth of bone tissue into the bone replacement material.

Figure 36:
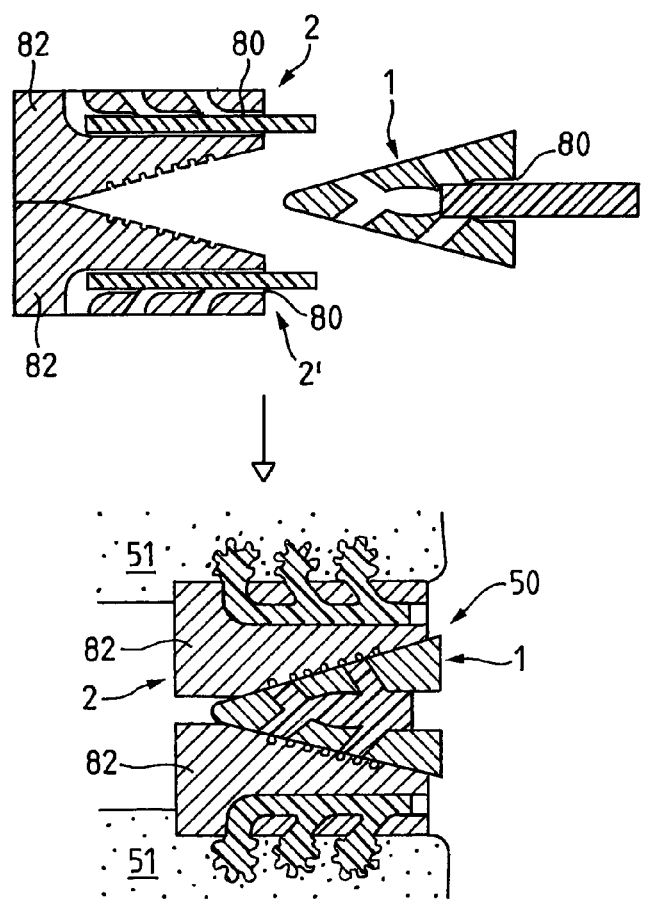
FIGS. 36 and 37 show a fourth group of embodiments of aspect B of the invention, wherein the base part serves to fix a based part relative to a further device part.
Figure 37:
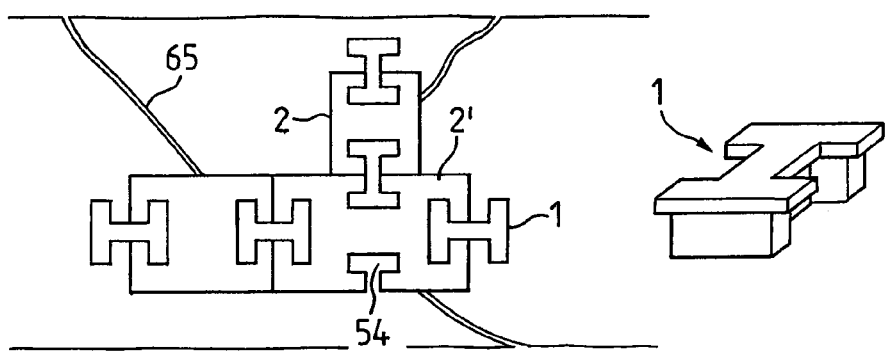

FIGS. 36 and 37 illustrate a further group of exemplary embodiments of aspect B of the invention, wherein a base part 1 serves for joining two based parts 2 and 2' which may be fixed to bone tissue with the aid of a liquefiable material and mechanical vibration and wherein the base part 1 is pushed between the two based parts and at the same time vibrated for liquefaction of a liquefiable material comprised by the base part 1 and for producing a positive fit connection between two opposite joining locations of the base part 1 and matched joining locations on the tow based parts 2 and 2'.

FIG. 36 shows a further exemplified embodiment of aspect B of the invention, wherein the device comprises a base part 1 and two further implant parts (based parts 2 and 2'). The device is in particular suitable as intervertebral element 50 for being implanted between two vertebral bodies 51 in order for the tow vertebral bodies to be fused together and to be spaced from each other in a predefined manner. FIG. 36 shows the base part 1 and the based parts 2 and 2' in section before implantation and assembly (above) and after implantation and assembly (below).

The two based parts 2 and 2' are shaped as an upper and a lower wedge 82 which wedges are equipped for being anchored in the end plates of the vertebral bodies 51 with the aid of a liquefiable material and mechanical vibration. The wedges 82 therefore comprise e.g. an inside channel 80 originating from a proximal face and ending in a plurality of mouths on the wedge surface to face the bone tissue of the vertebral body. The wedges 82 (perforated sleeves in wedge form) are made of a non-liquefyable material and the liquefiable material is positioned in the inside channels 80 and serves for anchoring the wedges 82 in the vertebral bone tissue.

The base part 1 to be pushed between the two based parts 2 and 2' is also wedge-shaped, comprises an inside channel 80 originating from the proximal face and ending in mouths on the surfaces to be in contact with the wedges 82, and it is made of a non-liquefiable material, the liquefiable material e.g. in form of a pin being positioned in the inside channel 80 and serving for joining the base part 1 to the based part wedges 82.

The based part wedges 82 are positioned between neighboring vertebral bodies and are anchored therein. For achieving such anchorage, mechanical vibration and pressure is applied to the pin of liquefiable material by applying a correspondingly shaped vibrating tool (not shown) to the proximal face of this pin. The wedge-shaped base part 2 is then introduced between the based part wedges 40 and brought into a position in which the distance between the vertebral bodies 51 is at the desired value. Then mechanical vibration and pressure is applied to the pin of liquefiable material in the inside channel 80 of the base part 1 by applying a correspondingly shaped vibrating tool (not shown) to the proximal face of this pin. By doing so, the liquefiable material in the base part 1 is at least partly liquefied and pressed through the mouths facing the based part wedges 82 (first joining location) to be pressed into undercut structures provided on the based part wedges 82 (second joining location, e.g. according to FIG. 5 or 6).

A wedge system similar to the wedge system shown in FIG. 36 may comprise two wedges only which both are anchored in the bone tissue of the vertebral bodies on one side and are joined to each other on an opposite side, this means an embodiment wherein the base part and the based part are substantially identical.

FIG. 37 shows a last embodiment of aspect B of the invention. Again more then one based part 2, 2' . . . is fixed relative to a bone surface with the aid of a plurality of base parts 1 which are laterally joined to the based parts 2 and at the same time are distally anchored in the bone tissue in which corresponding openings are provided. The based parts 2, 2' . . . are modular elements of a supporting plate which is e.g. used for osteosynthesis, in particular for fixing bone fragments 11.1 and 11.2 on either side of a bone fracture 65 relative to each other. As discussed in connection with FIG. 34 the lateral channels 54 provided at lateral sides of the plate elements preferably have undercut cross sections serving a second joining locations. The base parts 1 comprise a cross section which corresponds to two aligned channels 54 and are e.g. made of the liquefiable material or are coated therewith.

It is obvious for one skilled in the art to combine features of the above described and illustrated embodiments of aspect B of the invention in different ways and therewith to create further embodiments which are still encompassed by the invention.

FIGS. 38 to 46 illustrate a first group of embodiments of aspect C of the invention, according to which a preferably pin- or plate-shaped base part 1 comprising at its distal end a joining location and preferably being equipped for being anchored in bone tissue a its lateral sides, is positioned through a corresponding through bore in bone tissue for its distal end to be in contact with the joining location of the based part 2. By application of pressure and vibration to the proximal face of the base part, the base part is anchored in the bone tissue of the tunnel walls and simultaneously joined to the based part such securing the base part relative to a surface of the bone tissue. If the base part is not equipped for being anchored in the bone tissue of the tunnel wall it needs to be equipped with alternative means (e.g. a head) for being retained in the tunnel.

Figure 38:
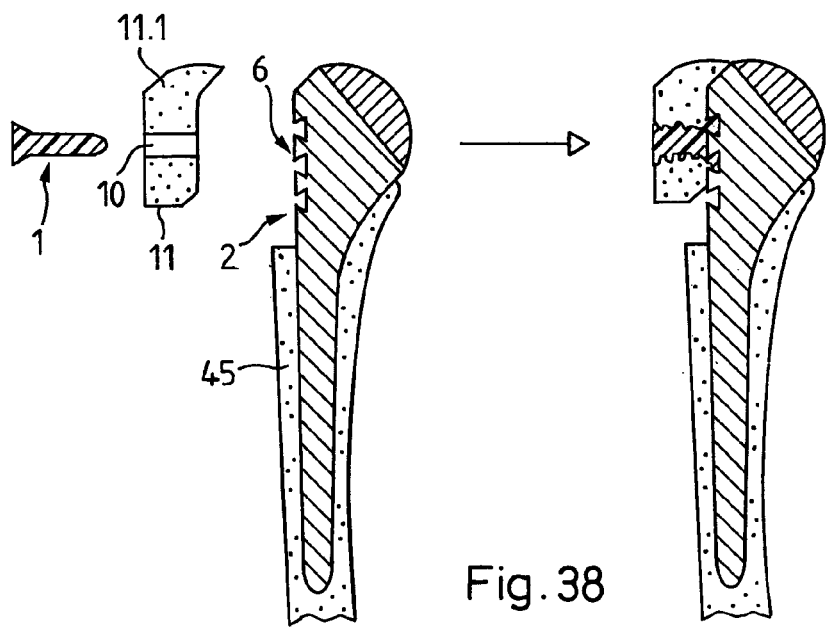
FIGS. 38 to 46 show a first group of embodiments of aspect C of the invention, wherein a based part is fixed relative to a bone surface by a base part which is introduced through the bone tissue beneath the bone surface to be joined to the based part and to be simultaneously anchored in the bone tissue with the aid of a liquefiable material and mechanical vibration.

FIG. 38 illustrates an exemplary embodiment of aspect C of the invention. The device is e.g. an endoprosthesis for replacement of a shoulder joint to which a bone fragment 11.1 is to be fixed. The endoprosthesis constitutes the based part 2 and a pin for fixing the bone fragment to the endoprosthesis is the base part 1. The bone fragment 11.1 is the bone tissue comprising a through opening 10. The base part 1 is equipped for being anchored in the bone tissue 11 of the bone fragment and preferably comprises the first joining location. The base part 1 is positioned through a proximal mouth of opening 10 for its distal end to get in contact with the joining location (preferably second joining location) of the based part 2 which is positioned against the distal mouth of the through opening 10. By applying pressure and vibration to the proximal face of the base part, the latter is anchored in the wall of the opening and simultaneously joined to the based part 2, i.e. the bone fragment is fixed relative to the endoprosthesis.

If the cross section of the through opening 10 is larger than the cross section of the base part 1 and/or if the proximal part of the base parts does not comprise a liquefiable material, no anchorage of the base part may occur or anchorage only in the region of the distal end thereof. For such a case it is advantageous to equip the base part 1 with a head section having a larger cross section which may be anchored on the surface of the bone fragment in the region of the proximal mouth of the through opening 10.

The shoulder joint endoprosthesis (based part 2) as shown in FIG. 38 e.g. consists of a non-liquefiable material such as titanium or a titanium alloy and is fixed in a correspondingly prepared tubular bone 45 using a known method such as e.g. cementing. The endoprosthesis is preferably equipped with the second joining location, e.g. a surface area with a structure as shown e.g. in any of FIG. 1 to 3, 4, 5 or 6. The base part 1 advantageously consists completely of the liquefiable material or comprises a non-liquefiable core being coated with the liquefiable material at least in surface areas serving as first joining location (distal end) and surface areas for anchoring the base part in bone tissue with the aid of the liquefiable material and mechanical vibration (lateral and/or proximal area).

For implanting the device according to FIG. 38, a through opening 10 is bored through the bone fragment 11.1. The fragment is then positioned against the endoprosthesis and possibly fixed temporarily using a clamp or glue. The base part is then positioned in the opening 10, its proximal end advantageously protruding therefrom. Mechanical vibration and pressure are then applied to the proximal face of the base part using e.g. a sonotrode with a distal face adapted to the proximal face of the base part. Due to liquefaction of the liquefiable material of the base part, the latter is simultaneously joined to the endoprosthesis and anchored in the bone tissue of the bone fragment 11.1.

The method as illustrated in FIG. 38 may be changed in various ways which leads to further embodiments of aspect C of the invention, such as e.g.:

The based part 2 (shoulder prosthesis) is equipped with the first joining location, e.g. carries a coat of the liquefiable material in surface areas to which bone fragments are likely to be fixed and the pin-shaped base part 1 is equipped with the second joining location, i.e. comprises in the area of its distal end a non-liquefiable material and preferably one undercut cavity or protrusion (e.g. according to FIG. 7).

The bone fragment 11.1 consists not of natural bone material but is a piece of bone replacement material having a similar porous structure as bone tissue which porous structure is suitable for being penetrated by the liquefied material of the base part.

The base part 1 may be designed to be a protrusion of the endoprosthesis and is anchored in the bone fragment by applying pressure and vibration to the bone fragment.

Figure 39:
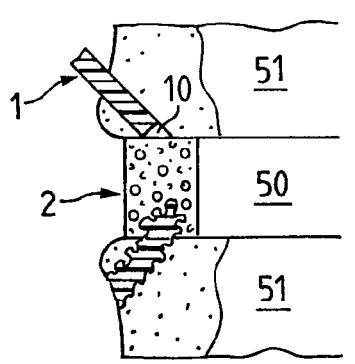

FIG. 39 illustrates a intervertebral element 50 (intervertebral fusion element, based part 2) positioned between two vertebral bodies 51 and comprising a lateral or frontal region of a porous material, e.g. a metal foam material (second joining location according to FIGS. 1 to 3). The intervertebral element 50 is secured between the vertebral bodies by two pin- or plate-shaped base parts 1 which are secured in the through openings 10 (tunnels) extending through the bone tissue of the vertebral bodies and are anchored therein and in the porous region of the intervertebral element (upper base part shown before application of pressure and vibration; lower base part shown after application of pressure and vibration).

Figure 40:
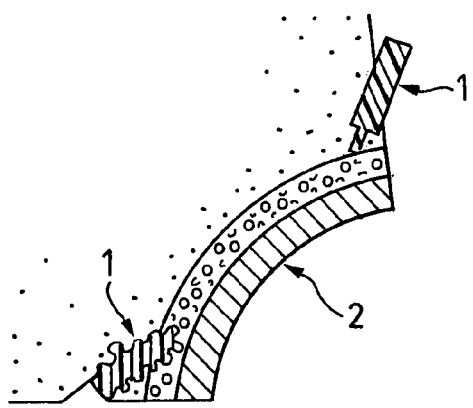

FIG. 40 shows an endoprosthesis (based part 2) suitable for resurfacing a concave bearing surface in a joint. The endoprosthesis is fixed relative to the bone with the aid of base parts 1 which extend through openings in the bone tissue and are joined to an inner layer of the endoprosthesis which consists e.g. of a metal foam material (second joining locations according to FIGS. 1 to 3). For better anchorage of the base part on the bone tissue it is advantageous to design the base part with a shoulder and the opening through the bone tissue with a corresponding step.

An endoprosthesis similar to the one shown in FIG. 40 may also replace a convex bearing surface of a joint.

Figure 41:
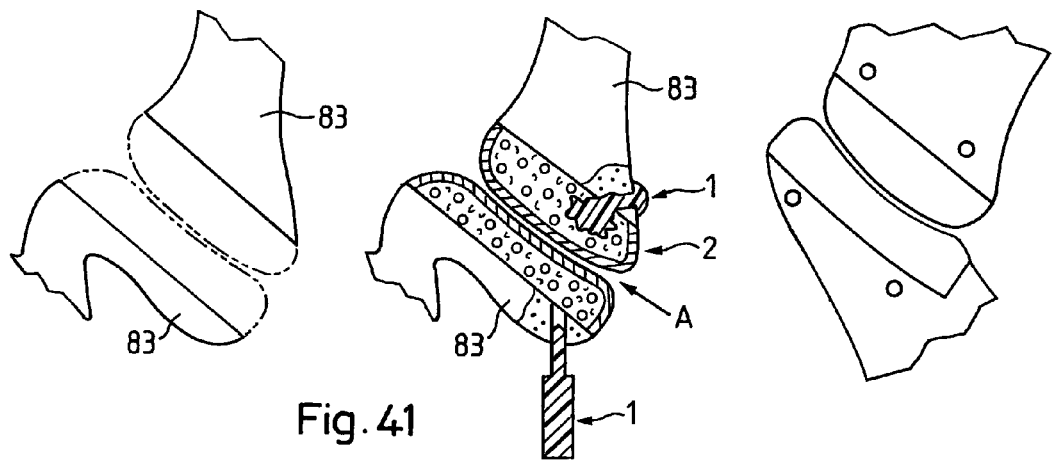

FIG. 41 illustrates a device for resurfacing of a facet joint according to aspect C of the invention. On the left of FIG. 41 the joint is shown in section with the bearing surface portions removed from the prosessus articularis inferior and superior 83. In the middle of FIG. 41 the bearing surface replacement parts (based parts 2) are shown in the same section, wherein the replacement parts comprise a porous inner section (metal foam constituting a second joining location as illustrated in FIGS. 1 to 3) and a full bodied outer layer constituting the bearing surface and wherein the replacement parts are fixed by pin-shaped base parts 1 which extend in openings extending through the bone tissue from dorsal sides of the processing articulates to the inner surface of the replacement parts (based parts 2) and are joined to the replacement part and preferably anchored in the bone tissue. The base parts 1 comprise a shoulder that is designed to reach the bone surface when the base part is pushed into the through opening and is able to be anchored in this bone surface or form a head protruding from the bone surface. On the right of FIG. 41, the implanted endoprostheses are shown viewed in the direction A as indicated in the section shown in the middle of FIG. 41.

Figure 42:
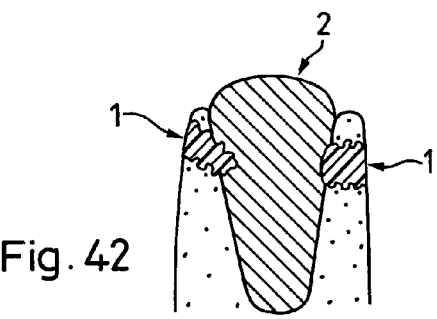

FIG. 42 shows a further embodiment of aspect C of the invention. The base part 2 of this embodiment is a joint prosthesis for a small joint like e.g. a finger or toe joint whose short stem is retained in a corresponding cavity provided in the epiphytic bone tissue of the corresponding bone end by a plurality of preferably pin-shaped base parts 1 which reach from opposite outside surfaces of the bone into the cavity and are laterally anchored in the bone tissue and distally joined to the implant (based part 2). Furthermore, the base parts 1 may fill empty space between the stem of the based part and the bone tissue. The based part comprises e.g. second joining locations according to FIGS. 1 to 3.

FIGS. 43 to 46 show a second group of exemplary embodiments of aspect C of the invention, for which embodiments the based part 1 is positioned in the marrow space of a tubular bone 45 and the base part 1 reaches from the outside of the tubular bone through the bone tissue of the tubular bone wall to the based part. For anchoring the base part in the wall of the tubular bone consisting of cortical bone tissue it may be advantageous to provide suitable structures in the opening through the bone wall.

Figure 43:
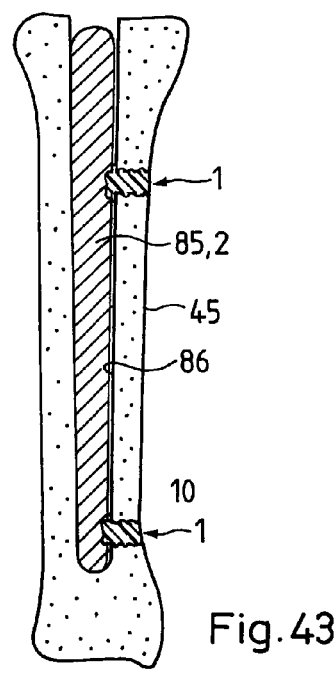

FIG. 43 shows a marrow nail or marrow plate 85 being fixed in the marrow space 86 of a tubular bone 45 with the aid of a plurality of preferably pin-shaped base parts 1 which preferably consist of the liquefiable material and which extend from the outside surface of the tubular bone 45 to the marrow space through openings 10 through the bone wall of the tubular bone to the marrow nail or plate 85. Such marrow nails or plates 85 are used for e.g. stabilizing a fracture of the tubular bone 45.

For implanting the device, openings 10 are provided and the marrow nail or plate 85 is introduced into the marrow space and possibly preliminarily retained with suitable means. The base parts 1 are then introduced into the openings 10 such that their distal end is in contact with the marrow nail or plate. Pressure and vibration applied to the proximal face of the base part results in joining the distal base part end to the marrow nail or plate 85 and possibly anchoring the base part in the bone wall of the tubular bone 45.

For embodiments as shown in FIG. 43 it may be that a space between the based part and the bone wall of the tubular bone in the region of the through opening provided for the base part has a shape, that when filled with the liquefiable material constitutes enough geometrical retention for a second joining location (similar to the one illustrated in FIG. 7) such that provision of a specific surface structure serving as second joining location may not be necessary.

Figure 44:
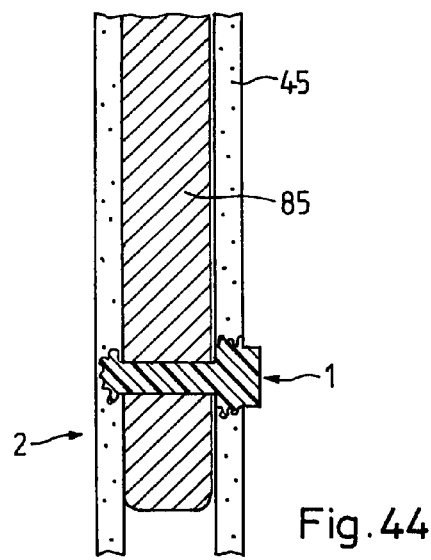

FIG. 44 shows a similar embodiment as FIG. 44. Instead of a joining location, the marrow nail or plate 85 comprises a through opening through which the base part 1 reaches to be in contact with the opposite wall of the tubular bone 45 to which wall the base part 1 is joined by being anchored therein. This means that in the embodiment according to FIG. 44 the opposite wall of the tubular bone 45 constitutes in the sense of the invention the based part 2.

Instead of a marrow nail or marrow plate 85 as illustrated in FIGS. 43 and 44, the based part of a similar embodiment may also be the shaft of a joint prosthesis which is to be retained in the marrow room of a tubular bone.

Figure 45:
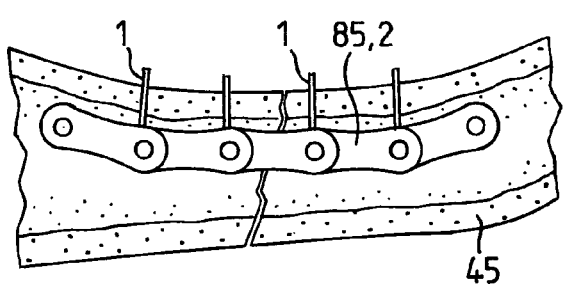

FIG. 45 shows a preliminarily flexible marrow nail 85 (based part 2) having the form e.g. of a link chain comprising links which are joined to each other in an articulate manner. As detailed in connection with the previously discussed embodiments of aspect C of the invention, the chain constitutes the based part 2 and each chain link or connecting element between chain links comprises a joining location which is fixed relative to the tubular bone in which the chain is positioned by being joined to the distal end of a preferably pin-shaped base part 1 reaching through the wall of the tubular bone 45 into the marrow space thereof to contact the chain. The preliminarily flexible chain can be introduced into the marrow space using considerably less room than introduction of a rigid marrow nail and when joined to the base parts 1 represents a rigid marrow nail having sufficient mechanical strength for its function.

Figure 46:
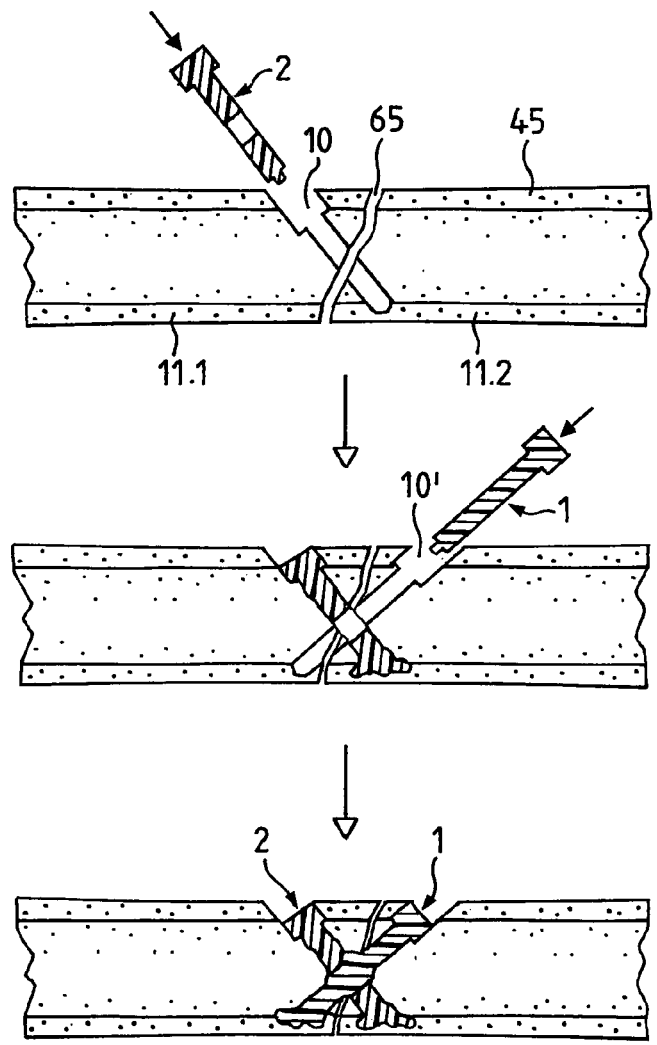

FIG. 46 shows a further embodiment of aspect C of the invention. The corresponding device again serves e.g. for stabilizing bone fragments 11.1 and 11.2 of a tubular bone 45 on two sides of a bone fracture 65. Other than in the previously discussed embodiments of aspect C the base part 1 and the based part 2 are quite similar, i.e. both are preferably pin-shaped and comprise the liquefiable material. The based part 2 is first introduced through an opening 10 in the bone wall such that its distal end reaches the opposite bone wall. With the aid of mechanical vibration and the liquefiable material, the based part 2 is anchored in the opening 10 and preferably on the inside surface of the opposite bone wall. The base part 1 is then introduced through a corresponding opening 10 which is positioned and oriented such that on introduction the base part 1 meets with the based part 2 in the marrow space before reaching the opposite bone wall. Pressure and vibration applied to the proximal end of the base part 1 results in anchoring the base part in the opening 10' and on the inside surface of the opposite bone wall as well as in joining the base part 1 to the based part 2 where they meet. For such joining, one of the parts is equipped with a second joining location, e.g. with a structured sleeve lining an opening in the based part 2 through which opening the base part 1 is introduced on meeting the based part.

Figure 47:
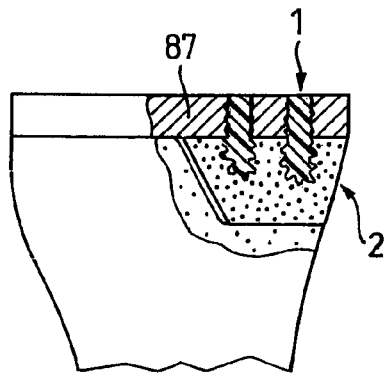

FIGS. 47 and 48 illustrate a second group of embodiments of aspect C of the invention. In these embodiments the again preferably pin-shaped base part 1, instead of being introduced through an opening in bone tissue, is introduced through an opening in a further device part for its distal end to be joined to the based part 2.

In the example as illustrated in FIG. 47, the further device part is e.g. a prosthetic tibia plateau 87 but may also be part of another orthopedic implant, e.g. for resurfacing another joint. The base part 1 serves for fixing a bone fragment (based part 2) or a corresponding piece of bone replacement material under the prosthetic tibia plateau 87, which both constitute porous non-liquefiable materials suitable for a second joining location (in the sense as e.g. illustrated in FIG. 1 to 3 or 4, 5, or 6). The base part 1 preferably consists of the liquefiable material, which, with the aid of mechanical vibration coupled into the proximal end of the base part 1, is liquefied and joined on the one hand to the base part 2 and to the tibia plateau. For the latter purposes the openings in the tibia plateau comprise inner surfaces equipped for forming a positive fit connection with the liquefiable material when re-solidified.

The prosthetic tibia plateau 87 is fixed in the place of the natural joint socket to be replaced using a per se known method, wherein the bone fragment (based part 2) is positioned thereunder before or after fixing the prosthetic plateau. The base part 1 (or a plurality of base parts) is positioned in the openings of the tibia plateau 87 and then mechanical vibration and pressure is applied to the proximal face of the base part. The base part 1 is therewith anchored in the bone fragment and simultaneously joined to the base part 1. It is possibly not necessary to provide a bore in the bone fragment for anchoring the base part 1 therein.

In the example as illustrated in FIG. 48 the further device part is an intervertebral element 50 for being positioned between to vertebral bodies 51 to replace an intervertebral disc or for fusing the two intervertebral discs. The based part is in this case the vertebral body 51 adjoining the intervertebral element 50. The intervertebral element is e.g. made of a non-liquefiable material and comprises at least one through opening whose proximal mouth is accessible from a front or lateral side of the vertebral column and whose distal mouth opens towards the bone tissue of the vertebral body 51. The through opening does not have a straight axis but a bent one, wherein the angle between the proximal part of the opening and the distal part is between 110 and 160 degrees or preferably between 135 and 150 degrees.

The intervertebral element 50 is positioned between two neighboring vertebral bodies 51. The base part 1 which is again preferably pin-shaped and consists of the liquefiable material is introduced into the opening in the intervertebral element 50 from the proximal mouth to the opening. It is then pressed towards the distal mouth of the opening and vibrated by a vibrating tool applied to its proximal end and therewith firstly bent to accommodate the bend in the opening and secondly anchored in the bone tissue of the vertebral body 51. The bend in the opening 10 and the base part 1 being bent accordingly suffice as positive fit connection for retaining the intervertebral element 50 in its position between the vertebral bodies 51.

It is obvious for one skilled in the art to combine features of the above described and illustrated embodiments of aspect C of the invention in different ways and therewith to create further embodiments which are still encompassed by the invention.

FIGS. 49 to 61 illustrate aspect D of the invention, according to which the device comprises a plurality of device parts which are pre-assembled such that they are moveable relative to each other in a limited manner, pre-assemblage being carried out in situ (in the implantation site) or ex situ. The pre-assembled device positioned in the implantation site is adapted to this site by further relative movement of the device parts to give the device a site-specific configuration which is then fixed by joining the device parts relative to each other. For this purpose the device parts are equipped with matched pairs of joining locations. The device parts are joined by pressing them against each other and by applying mechanical vibration to selected ones of them. Therein selected ones of the device parts may be further equipped for being anchored in bone tissue such representing base parts in the sense of the invention. However, this is not a condition for aspect D of the invention.

FIGS. 51 to 54 illustrate a first group of embodiments of aspect D of the invention. In these embodiments pairs of the device parts comprise matched pairs of first and second joining locations which, for fixing the site-specific configuration of the device, are joined together by application of mechanical vibration to one device part of the pair.

FIGS. 49 and 50 show an exemplary embodiment of aspect D of the invention. The corresponding device is a multi-part device comprising a plurality of device parts 90 being pre-assembled. The device in its pre-assembled configuration (FIG. 49 top) is a flexible chain of a plurality of device parts which are arranged to form in the implanted and assembled configuration e.g. an arc- or ring-shaped device anchored e.g. in the end plate of a vertebral body 51 and serving for retaining a natural or artificial intervertebral disc 50 or part thereof (FIG. 49 below: viewed from the side; FIG. 50: viewed from above).

The device parts 90 of the embodiment according to FIGS. 49 and 50 are all identical or quite similar and substantially all of them constitute at the same time a base part 1 and a based part 2. Each one of the device parts is (as base part 1) anchored in the bone tissue of the vertebral body 51 and joined to a neighboring device part (based part 2) part in preferably one only step of applying pressure and vibration. The named neighboring device part serves as base part in a following step of applying pressure and vibration.

All device parts 90 are equipped with a first and a second joining location 3 and 6 or alternating with two first or two second joining locations and they are further equipped with a contact location 7 and with liquefiable material positioned for anchoring the device part in the bone tissue. The pairs of matched joining locations are arranged on sides of the device parts which face each other. The parts have, as shown in FIG. 49, e.g. a trapezoidal form and the chain of device parts can be formed into a circle in which each part is in contact with and eventually joined to two neighboring device parts.

The flexible chain of preliminarily assembled device parts 90 as shown on the top of FIG. 49 is brought to the implantation site by e.g. minimal invasive surgery. The chain is very suitable for such surgery as it is flexible and may be realized having a much smaller cross section than the device in its implanted and finally assembled state shown in the bottom part of FIG. 49 and in FIG. 50. The chain is then positioned and implanted and assembled part after part. FIG. 49 (bottom) shows three positioned, implanted and assembled device parts forming an implant having the shape of an arc. FIG. 50 shows a corresponding ring-shaped device of eight device parts.

As vibrating tool for assembling the links of the chain shown in FIG. 49, a vibrating cable is applicable. The cable passes in the direction of the chain length through all chain links and its one end protrudes from the most distal one of the chain links. For pre-assembling the chain in a circle as illustrated in FIG. 50, the one cable end protruding from the most distal chain link is brought near the most proximal chain link and possibly slideably fixed to the cable protruding from the most proximal chain link, to form a chain ring having a still variable form. The proximal end of the cable is connected to a vibration source (e.g. ultrasonic device) and is then pulled away from the chain ring which is held in position with suitable means. Thereby the chain ring diameter is brought to a minimum and the links are pressed against each other. This pressure and the vibration of the cable result in the links being connected to each other by the matched pairs of joining locations being joined. If the cable has a surface structure which can function as a second joining location, the cable is at the same time joined to the inside of the links and a cable ring, when separated from the proximal rest of the cable can remain in the chain to form a further device part stabilizing and strengthening the chain ring.

Figure 51:
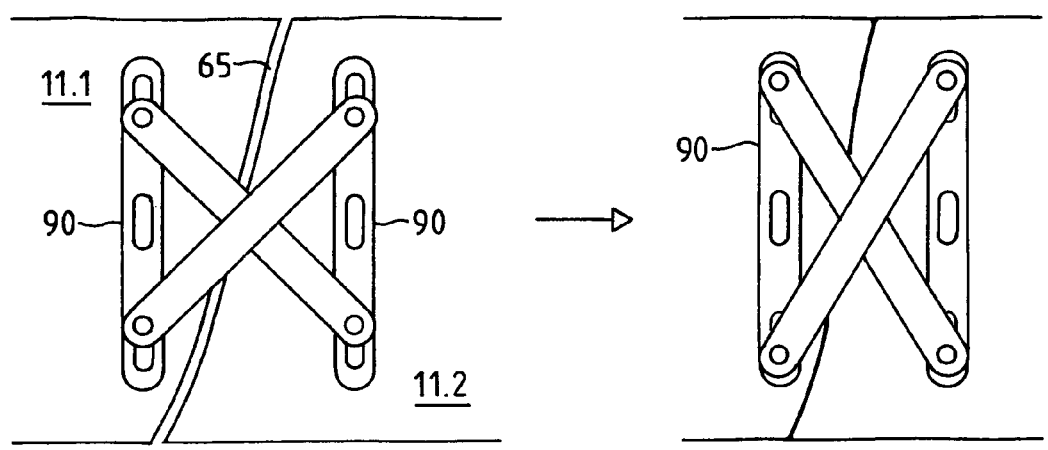

FIG. 51 shows a further multi-part device according to aspect D of the invention. The device comprises four device parts 90, which are pre-assembled in an articulating harmonica-like manner, wherein the device parts in the region of the articulating connections are equipped with matched pairs of first and second joining locations. The device serves e.g. for stabilizing two bone fragments 11.1 and 11.2 on either side of a bone fracture 65. For implanting the device, one of the four pre-assembled device parts 90 is fixed on either side of the fracture 65, e.g. by pins 91 which are anchored in the bone tissue of each bone fragment 11.1 and 11.2. The bone fragments or the fixed device parts respectively are then pressed against each other for closing the fracture 65 and the articulating connections between the device parts 90 are locked with the aid of mechanical vibration applied to each one of the connections.

It is possible to equip the device parts 90 of the device according to FIG. 51, which are situated nearer the bone tissue with pin-shaped protrusions facing towards the bone surface and comprising a liquefiable material. These protrusions can then be anchored in the openings in the bone tissue provided for such anchoring. Such equipped device parts then function as base parts in the sense of the earlier described aspects of the invention which base parts are simultaneously fixed to another device part (based part) and anchored in the bone tissue.

Figure 52:
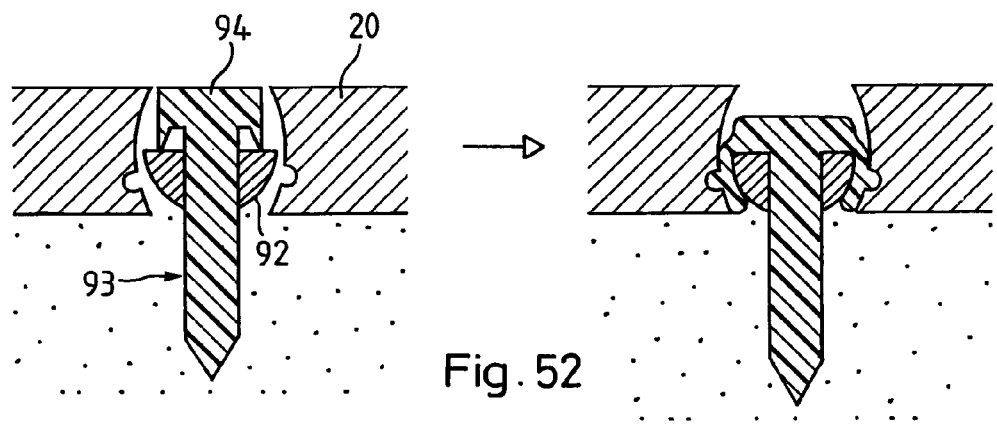
Figure 53:
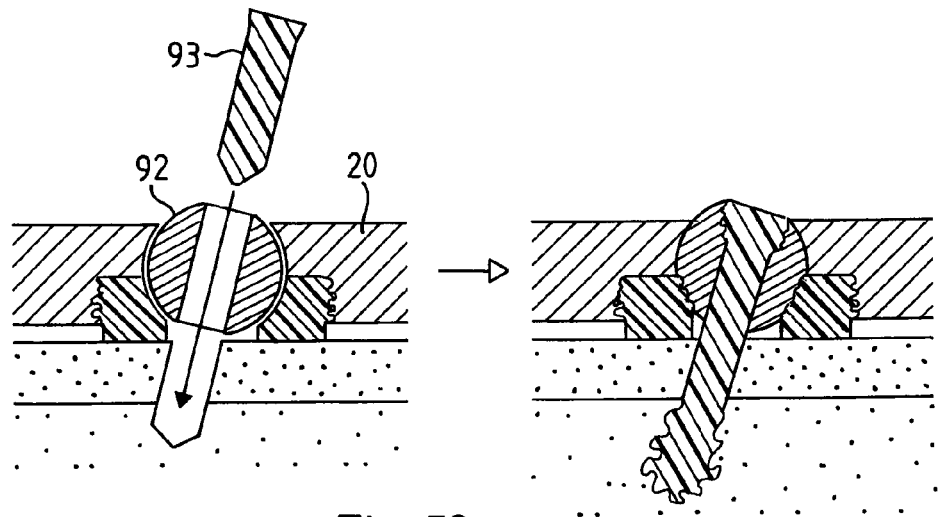

FIGS. 52 and 53 show further embodiments of aspect D of the invention. The three-part devices comprise a plate 20, applicable in osteosynthesis e.g. for stabilizing a bone fracture, and an insert 92 comprising with a through bore and being mounted in a through opening of the plate 20 to be capable to be oriented in different directions relative to the plate. The device further comprises a pin part 93 adapted in cross section to the opening in the insert 92. For implantation the plate 20 is positioned relative to a bone surface, the bone surface is provided with openings for the pin part by introducing a drill through the insert opening thereby orienting the insert 92 in a site-specific way and then introducing the pin part 93 through the opening in the insert 92 into the opening in the bone surface and applying pressure and vibration to its proximal face to firstly anchor the pin part 93 in the bone tissue and to secondly join the insert 92 to the plate 20 to fix it in the site-specific orientation.

According to FIG. 52, the bowl-shaped opening reaching through the plate 20 and the insert 92 formed as a half sphere comprise second joining locations each and the pin part 93 comprises a head region 94 consisting of a liquefiable material which material on pressing the pin part 93 into the openings is pushed between plate 20 and insert 92 to constitute first joining locations on either side and to fix the insert 92 relative to the plate 20.

According to FIG. 53 the pin part 93 and the plate 20 comprise the liquefiable material (first joining location) and the sphere-shaped insert 92 comprises the second joining location, preferably on surfaces facing the plate and on surfaces facing the pin part 93.

On pressing the pin part 93 extending through the opening in insert 92 into the opening in the bone tissue and vibrating it by applying a vibrating tool to its proximal face, the pin part is anchored in the bone tissue, the insert is joined in its site-specific orientation to the plate 20 and the pin part 93 is joined to the insert 92.

Figure 54:
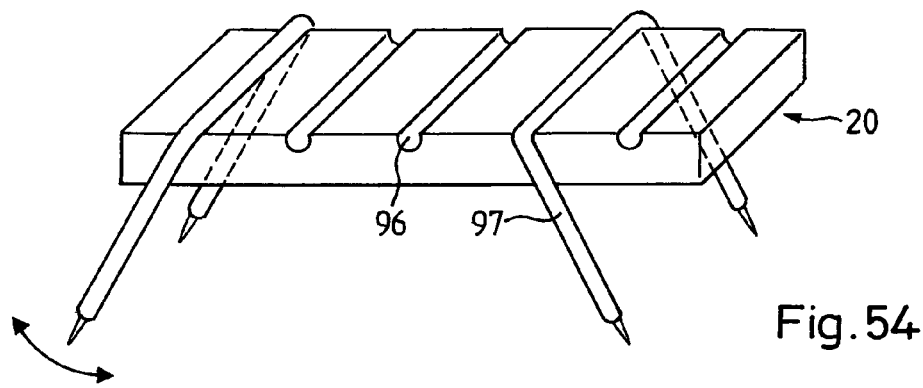

FIG. 54 shows a further pre-assembled device comprising a plate 20 (e.g. suitable foe osteosynthesis purposes) and means for fixing the plate relative to a bone surface. The plate 20 comprises a non-liquefiable material and within this material grooves 96 running across the plate-side facing away from the bone surface. The grooves are preferably undercut and comprise an inside surface suitable as second joining locations (e.g. rough surface, microgrooves). The means for fastening the plate 20 relative to bone tissue are staple-shaped device parts 97 e.g. comprising a metal wire as a core, which metal wire is at least partially coated with a liquefiable material except for the end regions where the metal core protrudes the coating and comprises cutting points or edges. The middle section of the staple-shaped device parts 97 has a cross section adapted to the groove cross section and a length greater than the groove length such that this middle section of the staple-shaped device part 97 can be snapped into one of the grooves and be pivoted therein (double arrow), such that the angle between the plate 20 and the staple-shaped device part 97 is freely selectable.

The arrangement of plate and pivoting staple-shaped device part constitute the pre-assembly. For fixing this pre-assembly relative to the bone surface the staple ends are forced into the bone tissue by applying pressure and mechanical vibration to the staple-shaped device part 97. This results in anchoring the side sections of the staple in the bone tissue and in joining its middle section to the plate 20.

FIGS. 55 to 61 illustrate a second group of embodiments of aspect D of the invention, in which the device, apart from the pre-assembly of device parts or the plurality of device parts designed for being pre-assembled, comprises at least one additional device part (locking part 100) which comprises a liquefiable material and is designed for being introduced between second joining locations facing each other in the pre-assembly of device parts. The site-specific configuration of the pre-assembled device parts is fixed by forcing the liquefiable material of the locking part (100) between the second joining locations of the pre-assembled device parts, wherein this material constitutes two opposite first joining locations matched to the second joining locations of the pre-assembled device parts.

The movement of the pre-assembled device parts relative to each other, which movement is to be blocked by the locking part 100 is in particular a rotation and/or an axial displacement of a rod or bar (moveable part 101) in a bearing opening in a bearing part 102 or formed by a plurality of bearing parts 102. Therein the bearing part 102 and/or the moveable part 102 comprise second joining locations facing each other when the movable part 101 is positioned in the bearing of the bearing part 102. The locking part 100 comprises the liquefiable material at a distal end. It is introduced through the bearing part 102 to contact the moveable part 101 and on application of pressure and mechanical vibration to its proximal face, the liquefiable material of its distal end is liquefied and pressed between the bearing part 102 and the moveable part 101 constituting on two opposite sides a first joining location matched to the two second joining location. On re-solidification the liquefiable material locks the moveable part 101 relative to the bearing part or parts 102.

Figure 55:
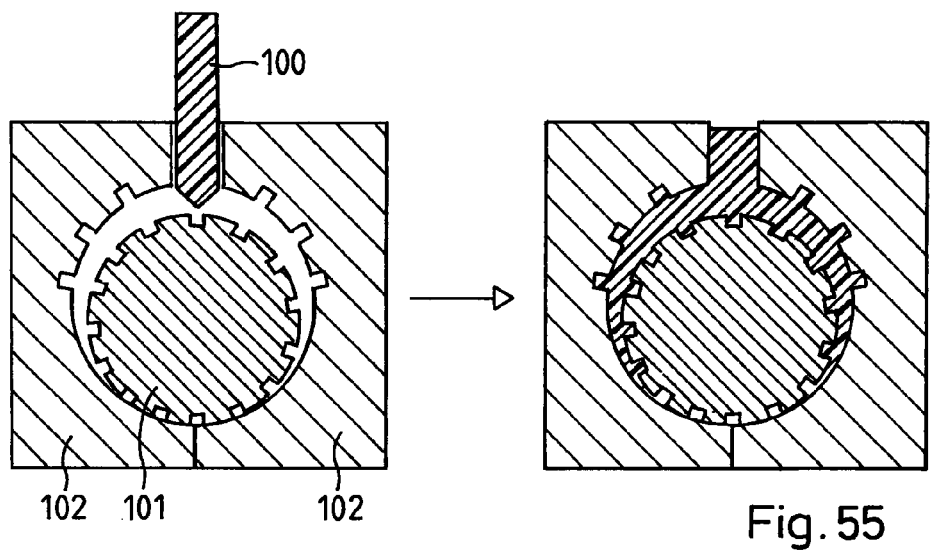

FIGS. 55 and 57 show the principle of the above referred to locking of a rotation and/or axial displacement of a rod (moveable part 101). The Figures are sections through bearing parts 102 and movable part 101 in a direction perpendicular to the rotation axis. Both bearing and movable part comprise in the sense of second joining locations depressions (as e.g. illustrated in FIG. 1-3, 4, 5 or 6). The space between bearing part 102 and moveable part 101 is accessible for the locking part 100, e.g. by the bearing part 102 comprising a corresponding opening leading from its outer surface to its bearing surface.

FIG. 55 shows two bearing parts 102 being connected in any suitable manner to close the bearing surface around the moveable part 101. For locking the moveable part 101 in a desired rotation and axial position relative to the bearing parts, the locking part 100 is introduced into the opening of the bearing part (left hand side of FIG. 55) and, by applying a vibrating tool to its proximal face, the locking part is vibrated and pressed against the surface of the movable part for the liquefiable material to be liquefied in the region of the distal end of the locking part and to be pressed between bearing parts and moveable part and into the structures serving as second joining locations (depressions). On re-solidification of the liquefiable material, rotation and/or axial displacement of the movable part 101 are prevented by the positive fit connection between the movable part 101 and the bearing parts 102 which positive fit connection is realized on opposite sides of the correspondingly shaped liquefiable material of the locking part (locked configuration: right hand side of FIG. 55).

Depending on the surface structures serving as second joining locations, the movable part 101 is locked regarding rotary and/or axial loads. Experiments using a bearing opening of 5.9 mm inner diameter and a rod 5.8 mm diameter being locked using a PLDLLA pin show good locking characteristics against axial displacement with annular grooves and against rotation with axial grooves. Good locking is achieved in both directions if the surface structure on the movable part 101 and the bearing parts 102 comprise a pattern of depressions or a combination of axial grooves or blind bores and ring-shaped grooves.

The locking principle as detailed above is achievable for axial loads only in the same manner for movable parts with other then round cross sections.

Figure 56:
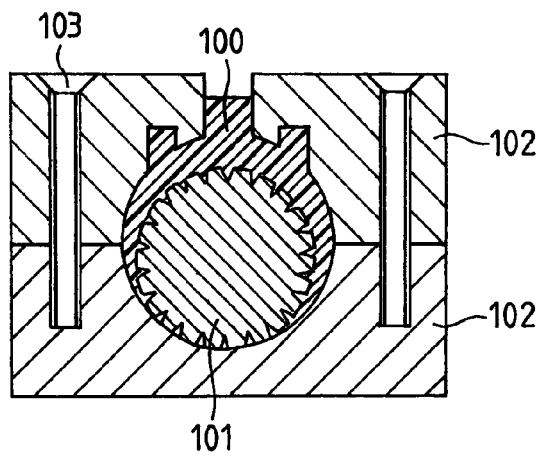

FIG. 56 shows a further embodiment of the locking according to aspect D of the invention, which locking in this case is reversible, if the connection between the bearing parts (e.g. threaded bolts in threaded bores 103) is reversible and if the liquefiable material of the locking part 100 does not wet the bearing surfaces and therefore does not adhere to these on re-solidification. For achieving reversibility of the locking, the structures of the second joining locations do not constitute undercuts in the direction, in which the bearing parts are to be separated from each other or constitute only small undercuts in this direction. Such structures are e.g. axial extending grooves whose cross section extends parallel to the bolts and bores 103 into the bearing surfaces of the bearing parts (as shown in FIG. 56) and relatively small structures (e.g. surface roughness) on the movable part 101. Obviously circular grooves as mentioned above are suitable for a reversible locking as illustrated in FIG. 56.

For loosening the connection between bearing parts 102 and movable part 101, the bolts 103 are loosened and the liquefiable material is removed to release the moveable part 101.

FIGS. 57 to 61 show exemplary applications of the locking principle according to aspect D of the invention.

FIGS. 57 and 58 show a rod lock application for fixing a rod (moveable part 101) to neighboring vertebral bodies 51 in order to support the vertebral column and maintain desired distances between the vertebral bodies. The rod locking device is substantially the device according to FIG. 56, wherein the non removable bearing part is equipped with a protrusion 105 which is e.g. equipped for the locking device to be anchored in a corresponding bore provided in the vertebral body. FIG. 57 shows the locking device closed around the rod in a larger scale and FIG. 58 shows the locking device mounted to a vertebral body.

FIG. 59 shows an external fixation device for stabilizing the fragments of a tubular bone 45 on both sides of a bone fracture 65. The device comprises supports 110 anchored with suitable means in the bone fragments and a rod 111 which connects the supports 111 to form together with them the exterior device. Between supports 110 and rod 111 double locking devices 112 are provided. A first bearing part 102.1 bears the support 110 and defines the axial and rotary position of the locking device relative to the support. A second bearing part 102.2 bears the rod 111 and defines the axial and rotary position of the rod relative to the support. A third bearing part 102.3 bears an axel of the first bearing part 102.1 and defines an angle between the support and the rod. The whole external fixation device is pre-assembled in situ. When all parts are assembled their relative positions and orientations are locked by introducing locking parts at all locations indicated with an arrow.

FIG. 60 shows a further application of a device which is similar to the device shown in FIG. 59 and serves for stabilizing a vertebral column and maintaining defined distanced between vertebral bodies 51. The supports in this case are pedicle screws.

Figure 61:
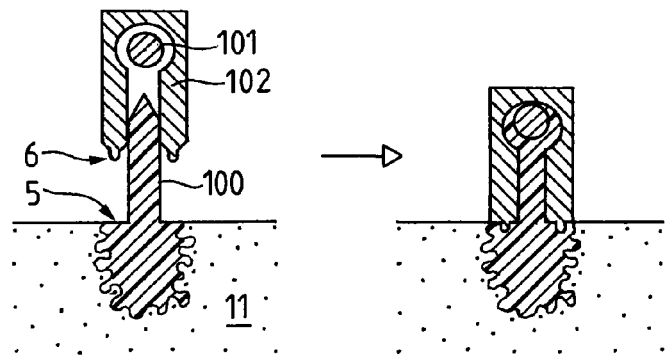

FIG. 61 shows in more detail a strikingly simple embodiment of a locking device according to aspect D of the invention. The device comprises a locking part 100, which preferably consists of the liquefiable material or is coated therewith, and which is anchored in bone tissue 11 with the aid of mechanical vibration. The locking part 100 comprises a shoulder on which a vibrating tool for its anchorage is applied and a protruding section of a smaller cross section. The bearing part 102 which is preferably made of a non-liquefiable material comprises an inner bearing surface and an opening leading to this bearing surface which opening is adapted to the protruding section of the locking part 100. The outer surface of the bearing part 102 around the opening is equipped for constituting a second joining location 6 (e.g. as illustrated in FIG. 6. The bearing part 102 is preliminarily positioned on the protruding section of the locking part 100 and the movable part 101 is introduced in the bearing part 102. The site-specific rotary and/or axial position of the movable part is established and then the bearing part is pushed towards the bone surface and simultaneously vibrated, whereby the protruding section of the locking part 100 is pushed against the moveable part 101, its liquefiable material is liquefied and penetrates between the moveable part 101 and the bearing part 102 to lock these two on re-solidification. At the same time, the end of the bearing part 102 which faces the bone surface is pressed into the shoulder of the locking part 100 and is joined to the latter in the sense of a further pair of matched first and second joining locations.

Instead of or in addition to the above described joining of the bearing part 102 to the locking part 100 via the shoulder of the locking part, it is possible also to equip the inside of the bearing part opening for the protruding section of the locking part 100 as second joining location and effect there a joint between the two parts.

It is obvious for one skilled in the art to combine features of the above described and illustrated embodiments of aspect D of the invention in different ways and therewith to create further embodiments which are still encompassed by the invention.

Figure 62:
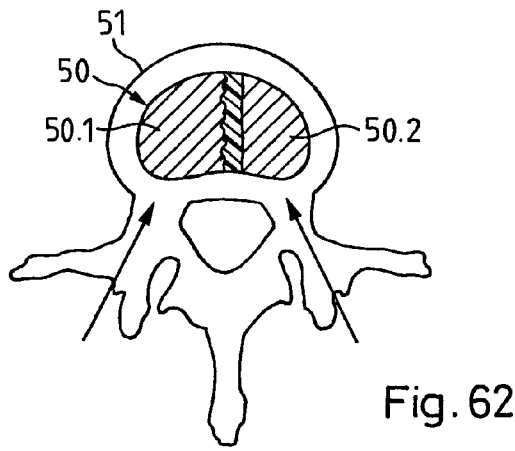
FIGS. 62 to 64 show exemplary embodiments of aspect E of the invention, wherein a plurality of device parts is assembled and joined in situ.
Figure 64:
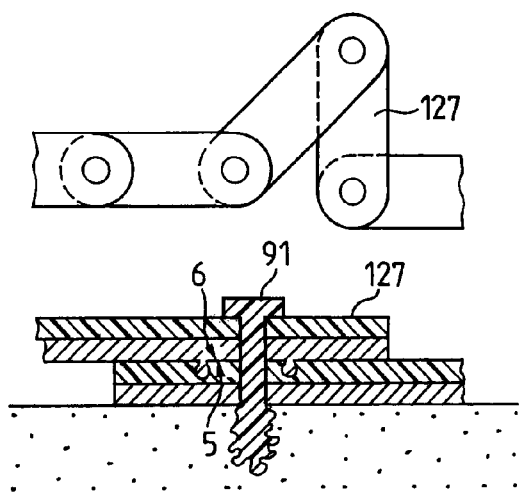
Figure 63:
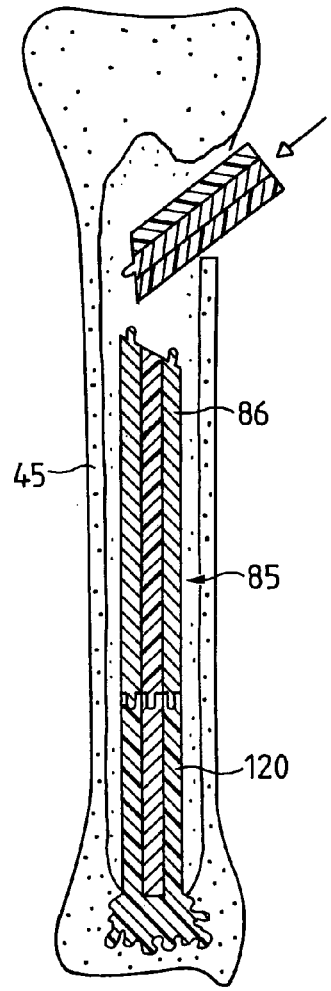

FIGS. 62 to 64 illustrate aspect E of the invention, according to which a plurality of device parts is brought independently to the implantation site to be joined in the implantation site to form the complete device. The device parts are equipped with matched pairs of first and second joining locations, they are positioned in the implantation site such that the joining locations of a matched pair are facing each other. The device parts are then joined to each other by being pressed against each other and by applying mechanical vibration to one of them. Therein selected ones of the device parts may be further equipped for being anchored in bone tissue with the aid of a of a liquefiable material and mechanical vibration such representing base parts in the sense of the invention. However, this is not a condition for aspect D of the invention.

FIG. 62 shows a first exemplary embodiment of aspect D of the invention. The device is a intervertebral element 50 (fusion element, e.g. cage) to be implanted between two vertebral bodies 51. The intervertebral element 50 comprises two halves 50.1 and 50.2, wherein each one of the halves comprises one of the joining locations of the matched pair thereof on the side where they are to be joined. The advantage of the intervertebral element according to FIG. 62 as compared with a one-piece intervertebral element is the fact that the element halves can be introduced between the vertebral bodies from dorsal-lateral sides (arrows), from where they can be pressed against each other as well. The pair of matched joining locations may be as illustrated in any one of FIG. 1 to 3, 4, 5, or 6.

FIG. 63 shows a second exemplary embodiment of aspect D of the invention. The device is a marrow nail 85 or plate which comprises e.g. three device parts to be introduced into the marrow space 86 of a tubular bone 45 in succession and to be assembled therein in tow joining steps. The first nail part 120 comprises e.g. a core of non-liquefiable material and a coat of liquefiable material and is anchored in the cancellous bone of the bone end with the aid of the liquefiable material and mechanical vibration and on the opposite face comprises a first joining location (coat) and a second joining location (core). The second device part comprises e.g. a core of liquefiable material and a coat of non-liquefiable material and on both end faces comprises a first and second joining location. The third device part substantially corresponds to the first device part and when introduced and joined to the second device part may be anchored in the diaphysic bone tissue of the bone end.

Due to the reduced length of the device parts of the nail 85 according to FIG. 63 compared with the complete length of the nail, a much smaller lateral opening in the bone is necessary for introducing the nail or its parts respectively than is the case for a known complete nail.

FIG. 64 shows a modular plate (top: arrangement of four plate modules 127 viewed from above; bottom: arrangement of two plate modules 127 in section) according to aspect D of the invention. The plate modules 127 are fixed to a bone surface with the aid of pins 91 which reach through bores of two superimposed plate modules and may be anchored in the bone tissue with the aid of a liquefiable material and mechanical vibration. Each plate module comprises at least two bores. The plate modules comprise in the area of the bores for the pins on one side a first joining location 5 and on the other side a second joining location 6. This is realized e.g. by plate modules comprising a layer of a liquefiable material and a layer of a non-liquefiable material, wherein the latter layer comprises a surface structure suitable for a second joining location, as e.g. shown in FIG. 5 or 6.

The modules are pre-arranged on the bone surface one after the other by drilling suitable openings for successive modules and positioning successive pins in the openings. When the whole plate is assembled and preliminarily fixed, the pins 91 are driven into the bone openings by applying mechanical vibration to their proximal face and are therewith anchored in the bone tissue. At the same time the plate modules 127 are joined together to stiffen and stabilize the modular arrangement.

It is obvious for one skilled in the art to combine features of the above described and illustrated embodiments of aspect E of the invention in different ways and therewith to create further embodiments which are still encompassed by the invention.

It is also obvious for one skilled in the art to use specific features of devices described in connection with one of the aspects of the invention in embodiments according to any other aspect of the invention.

The invention claimed is:

1. A method for implanting and assembling a device in a patient, the method, comprising the steps of:

providing at least one base part of the device, the base part comprising a liquefiable material, and a based part of the device, wherein the based part comprises a based part joining location, the based part joining location having an associated structure that is suitable to form a positive fit connection with the liquefiable material, positioning the based part relative to bone tissue, with the based part joining location and associated structure being spaced from, but facing toward, the bone tissue;

inserting the base part into a space between the based part joining location and the bone tissue by pushing the base part between the bone tissue and the based part joining location and associated structure;

coupling vibration into the base part through a proximal face thereof for a time sufficient for liquefying at least part of the liquefiable material to yield liquefied material;

pressing a first portion of the liquefied material into the bone tissue while a second portion of the liquefied material flows into and is received by the associated structure of the based part joining location, and letting the liquefied material re-solidify to yield the positive fit connection between the based part and the bone tissue via the base part.

2. The method according to claim 1, wherein the step of pushing comprises cutting into the bone surface with self-reaming structures provided on the base part.

3. The method according claim 1, wherein the step of positioning comprises positioning the based part in an opening provided in the bone tissue and wherein the step of pushing comprises pushing the base part into the opening beside the based part.

4. The method according to claim 3, wherein the opening comprises an undercut bottom and wherein the based part comprises a distal protrusion which is positioned in the undercut bottom.

5. The method according to claim 3, wherein a plurality of base parts are pushed into the opening beside the based part.

6. The method according to claim 1, wherein channels are provided in a bone surface and/or in the based part.

7. The method according to claim 1, wherein a bone surface is the face of a vertebral body or the inside surface of a tubular bone.

8. The method according to claim 1, wherein the based part comprises bone tissue which constitutes a second joining location.

9. The method according to claim 8, wherein the based part is tendon-bone graft to be fixed in a bone opening or tunnel or a bone fragment to be fixed relative to a further bone fragment, the two bone fragments being separated by a bone fracture.

10. A device to be implanted and assembled in a patient with the method according to claim 1, the device comprising a base part being equipped for being anchored in bone tissue of the patient with the aid of a first liquefiable material and mechanical vibration, and a based part, wherein of the two device parts each one comprises one of a pair of matched joining locations, wherein a first one of the two joining locations comprises a second liquefiable material and a second one of the two joining locations comprises a non-liquefiable material and a structure which is suitable to form a positive fit connection with the second liquefiable material, wherein the joining location of the base part is situated at a first lateral side thereof and the base part is equipped for being anchored in the bone tissue on a second lateral side thereof and wherein the joining location of the based part is situated at a lateral side thereof.

11. The device according to claim 10, wherein the first and second liquefiable materials are the same material, wherein the base part comprises the first joining location and wherein the base part consists of said same material or comprises a core of a non-liquefiable material coated at least partly with said same material or comprises a perforated sleeve in which said same material is positioned.

12. The device according to claim 10, wherein the device is pin-, plate- or wedge-shaped.

13. The device according to claim 11, wherein the core or perforated sleeve comprises self-reaming structures.

14. The device according to claim 10, wherein the based part is equipped for fixing a suture, wire, rod or a further device part.

15. The device according to claim 10, wherein the based part is an intervertebral fusion or non-fusion element.

16. The device according to claim 10, wherein the based part is pin-shaped and comprises a head and the base part is wedge-shaped and designed to be pushed between the head and a surface of a bone tissue in which the based part is to be positioned and fixed.

17. The device according to claim 10, wherein the based part is designed to be introduced in a marrow space of a tubular bone.

* * * * *